United States Patent
Azuma et al.

(10) Patent No.: US 10,795,273 B2
(45) Date of Patent: Oct. 6, 2020

(54) BIS-BUTADIENE DERIVATIVE AND ELECTROPHOTOGRAPHIC PHOTOSENSITIVE MEMBER

(71) Applicant: KYOCERA Document Solutions Inc., Osaka (JP)

(72) Inventors: Jun Azuma, Osaka (JP); Kensuke Kojima, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/443,624

(22) Filed: Jun. 17, 2019

(65) Prior Publication Data

US 2019/0384190 A1 Dec. 19, 2019

(30) Foreign Application Priority Data

Jun. 19, 2018 (JP) ................................ 2018-116363

(51) Int. Cl.
*G03G 5/06* (2006.01)
*C07C 211/54* (2006.01)
*G03G 5/05* (2006.01)

(52) U.S. Cl.
CPC .......... *G03G 5/0614* (2013.01); *C07C 211/54* (2013.01); *G03G 5/056* (2013.01);
(Continued)

(58) Field of Classification Search
CPC ........................... G03G 5/0564; G03G 5/0614
See application file for complete search history.

(56) References Cited

U.S. PATENT DOCUMENTS

| 5,686,212 A | 11/1997 | Tomiuchi et al. |
| 2005/0008957 A1* | 1/2005 | Ikegami ................. G03G 5/051 430/56 |

(Continued)

FOREIGN PATENT DOCUMENTS

| JP | H06-118674 A | 4/1994 | |
| JP | 2001-1133995 | * 5/2001 | ............... G03G 5/06 |

OTHER PUBLICATIONS

Translation of JP 2001-1133995.*

*Primary Examiner* — Peter L Vajda
(74) *Attorney, Agent, or Firm* — Studebaker & Brackett PC

(57) ABSTRACT

A bis-butadiene derivative is represented by general formula (1) shown below.

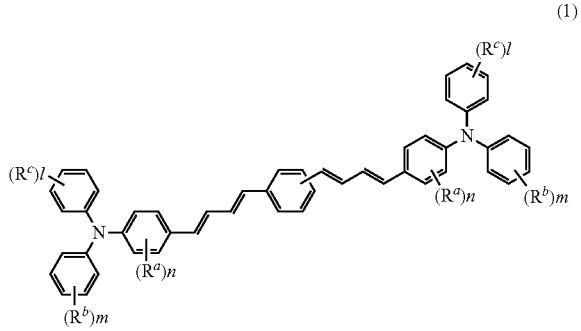

In general formula (1), Ra, Rb, and Rc each represent, independently of one another, an alkyl group having a carbon number of at least 1 and no greater than 8 or an alkoxy group having a carbon number of at least 1 and no
(Continued)

greater than 8. l and m each represent, independently of one another, an integer of at least 0 and no greater than 5. n represents an integer of at least 0 and no greater than 4. Chemical groups Ra may be the same as or different from each other. Chemical groups Rb may be the same as or different from each other. Chemical groups Rc may be the same as or different from each other.

8 Claims, 2 Drawing Sheets

(52) U.S. Cl.
CPC ......... *G03G 5/0564* (2013.01); *G03G 5/0609* (2013.01); *G03G 5/0612* (2013.01); *G03G 5/0661* (2013.01); *C07C 2601/16* (2017.05)

(56) References Cited

U.S. PATENT DOCUMENTS

| | | | | |
|---|---|---|---|---|
| 2006/0160005 | A1* | 7/2006 | Kuboshima | G03G 5/0517 430/96 |
| 2007/0054209 | A1* | 3/2007 | Azuma | G03G 5/0517 430/73 |
| 2016/0357118 | A1* | 12/2016 | Tsurumi | G03G 5/0614 |
| 2018/0046098 | A1* | 2/2018 | Shimizu | G03G 5/056 |

* cited by examiner

BIS-BUTADIENE DERIVATIVE AND ELECTROPHOTOGRAPHIC PHOTOSENSITIVE MEMBER

INCORPORATION BY REFERENCE

The present application claims priority under 35 U.S.C. § 119 to Japanese Patent Application No. 2018-116363, filed on Jun. 19, 2018. The contents of this application are incorporated herein by reference in their entirety.

BACKGROUND

The present disclosure relates to a bis-butadiene derivative and an electrophotographic photosensitive member.

Electrophotographic photosensitive members are used in electrographic image forming apparatuses. Examples of the electrophotographic photosensitive members include a multi-layer electrophotographic photosensitive member and a single-layer electrophotographic photosensitive member. The multi-layer electrophotographic photosensitive member includes, as a photosensitive layer, a charge generating layer having a charge generation function and a charge transport layer having a charge transport function. The single-layer electrophotographic photosensitive member includes, as a photosensitive layer, a single-layer photosensitive layer having a charge generation function and a charge transport function.

In an example, the electrophotographic photosensitive member includes a photosensitive layer. The photosensitive layer contains for example a compound having a bis-stilbene structure represented by chemical formula (h-3) shown below as a charge transport material.

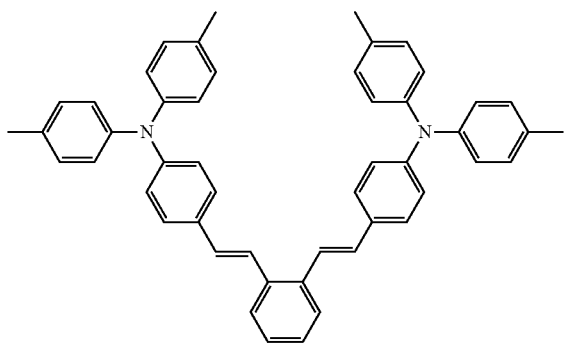

(h-3)

SUMMARY

A bis-butadiene derivative according to an aspect of the present disclosure is represented by general formula (1) shown below.

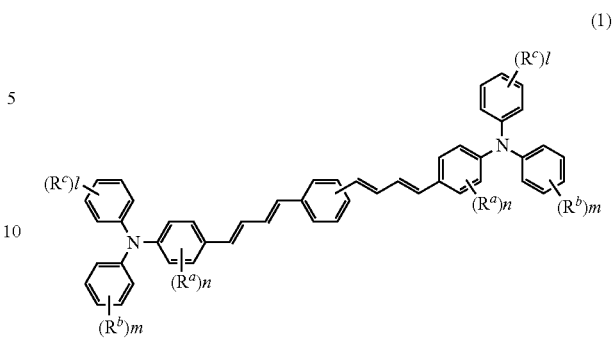

(1)

In general formula (1), $R^a$, $R^b$, and $R^c$ each represent, independently of one another, an alkyl group having a carbon number of at least 1 and no greater than 8 or an alkoxy group having a carbon number of at least 1 and no greater than 8. l and m each represent, independently of one another, an integer of at least 0 and no greater than 5. n represents an integer of at least 0 and no greater than 4. Plural chemical groups $R^a$ may be the same as or different from each other. Plural chemical groups $R^b$ may be the same as or different from each other. Plural chemical groups $R^c$ may be the same as or different from each other. Plural indices l may be the same as or different from each other. Plural indices m may be the same as or different from each other. Plural indices n may be the same as or different from each other.

An electrophotographic photosensitive member according to an aspect of the present disclosure includes a conductive substrate and a photosensitive layer located either directly or indirectly on the conductive substrate. The photosensitive layer contains at least a charge generating material, a charge transport material, and a binder resin. The charge transport material includes the bis-butadiene derivative.

DETAILED DESCRIPTION

Figure 1:
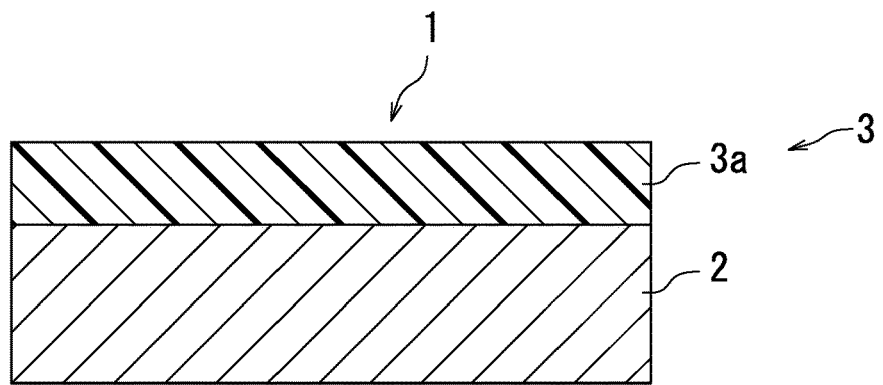
FIG. 1 is a cross-sectional view of an example of an electrophotographic photosensitive member according to a third embodiment of the present disclosure.

The following describes embodiments of the present disclosure in detail. However, the present disclosure is by no means limited to the following embodiments.

The present disclosure can be practiced within a scope of objects of the present disclosure with alterations made as appropriate. Although some overlapping explanations may be omitted as appropriate, such omission does not limit the gist of the present disclosure.

In the following description, the term "-based" may be appended to the name of a chemical compound to form a generic name encompassing both the chemical compound itself and derivatives thereof. When the term "-based" is appended to the name of a chemical compound used in the name of a polymer, the term indicates that a repeating unit of the polymer originates from the chemical compound or a derivative thereof.

Hereinafter, a halogen atom, an alkyl group having a carbon number of at least 1 and no greater than 8, an alkyl group having a carbon number of at least 1 and no greater than 6, an alkyl group having a carbon number of at least 1 and no greater than 5, an alkyl group having a carbon number of at least 1 and no greater than 4, an alkyl group having a carbon number of at least 1 and no greater than 3, an alkoxy group having a carbon number of at least 1 and no greater than 8, an alkoxy group having a carbon number of at least 1 and no greater than 6, an alkoxy group having a carbon number of at least 1 and no greater than 3, an aryl group having a carbon number of at least 6 and no greater than 14, an aryl group having a carbon number of at least 6 and no greater than 10, an aralkyl group having a carbon number of at least 7 and no greater than 15, an aralkyl group having a carbon number of at least 7 and no greater than 11, and a heterocyclic group each refer to the following, unless otherwise stated.

Examples of the halogen atom (a halogen group) include a fluorine atom (a fluoro group), a chlorine atom (a chloro group), a bromine atom (a bromo group), and iodine atom (an iodo group).

The alkyl group having a carbon number of at least 1 and no greater than 8, the alkyl group having a carbon number of at least 1 and no greater than 6, the alkyl group having a carbon number of at least 1 and no greater than 5, the alkyl group having a carbon number of at least 1 and no greater than 4, and the alkyl group having a carbon number of at least 1 and no greater than 3 each are an unsubstituted straight chain or branched chain alkyl group. Examples of the alkyl group having a carbon number of at least 1 and no greater than 8 include a methyl group, an ethyl group, an n-propyl group, an isopropyl group, an n-butyl group, a sec-butyl group, a tert-butyl group, an n-pentyl group, an isopentyl group, a neopentyl group, a 1,2-dimethylpropyl group, a straight chain or branched chain hexyl group, a straight chain or branched chain heptyl group, and a straight chain or branched chain octyl group. Examples of the alkyl group having a carbon number of at least 1 and no greater than 6, the alkyl group having a carbon number of at least 1 and no greater than 5, the alkyl group having a carbon number of at least 1 and no greater than 4, and the alkyl group having a carbon number of at least 1 and no greater than 3 are respectively the groups having a carbon number of at least 1 and no greater than 6, the groups having a carbon number of at least 1 and no greater than 5, the groups having a carbon number of at least 1 and no greater than 4, and the groups having a carbon number of at least 1 and no greater than 3 among the groups listed as the examples of the alkyl group having a carbon number of at least 1 and no greater than 8.

Each of the alkoxy group having a carbon number of at least 1 and no greater than 8, the alkoxy group having a carbon number of at least 1 and no greater than 6, and the alkoxy group having a carbon number of at least 1 and no greater than 3 is an unsubstituted straight chain or branched chain alkoxy group. Examples of the alkoxy group having a carbon number of at least 1 and no greater than 8 include a methoxy group, an ethoxy group, an n-propoxy group, an isopropoxy group, an n-butoxy group, a sec-butoxy group, a tert-butoxy group, an n-pentoxy group, an isopentoxy group, a neopentoxy group, a hexoxy group, a heptoxy group, and an octoxy group. Examples of the alkoxy group having a carbon number of at least 1 and no greater than 6 and the alkoxy group having a carbon number of at least 1 and no greater than 3 are respectively the groups having a carbon number of at least 1 and no greater than 6 and the groups having a carbon number of at least 1 and no greater than 3 among the groups listed as the examples of the alkoxy group having a carbon number of at least 1 and no greater than 8.

Each of the aryl group having a carbon number of at least 6 and no greater than 14 and the aryl group having a carbon number of at least 6 and no greater than 10 is an unsubstituted aryl group. Examples of the aryl group having a carbon number of at least 6 and no greater than 14 include a phenyl group, a naphthyl group, an indacenyl group, a biphenylenyl group, an acenaphthylenyl group, an anthryl group, and a phenanthryl group. Examples of the aryl group having a carbon number of at least 6 and no greater than 10 include a phenyl group and a naphthyl group.

Each of the aralkyl group having a carbon number of at least 7 and no greater than 15 and the aralkyl group having a carbon number of at least 7 and no greater than 11 is an unsubstituted aralkyl group. Examples of the aralkyl group having a carbon number of at least 7 and no greater than 15 include an alkyl group having a carbon number of at least 1 and no greater than 6 and substituted by an aryl group having a carbon number of at least 6 and no greater than 14. Examples of the aralkyl group having a carbon number of at least 7 and no greater than 11 include an alkyl group having a carbon number of at least 1 and no greater than 3 and substituted by an aryl group having a carbon number of at least 6 and no greater than 10.

Examples of the heterocyclic group include a heterocyclic group having at least 5 members and no greater than 14 members. The heterocyclic group having at least 5 members and no greater than 14 members is an unsubstituted heterocyclic group having carbon atoms and at least one hetero atom. The at least one hetero atom includes one atom selected from the group consisting of a nitrogen atom, a sulfur atom, and an oxygen atom. Examples of the heterocyclic group having at least 5 members and no greater than 14 members include a heterocyclic group having a monocyclic heterocyclic ring having 5 members or 6 members (also referred to below as a heterocyclic ring (H)) and including carbon atoms and at least 1 and no greater than 3 hetero atoms; a heterocyclic group in which two heterocyclic rings (H) are fused; a heterocyclic group in which a heterocyclic ring (H) and a monocyclic hydrocarbon ring having 5 members or 6 members are fused; a heterocyclic group in which three heterocyclic rings (H) are fused; a heterocyclic group in which two heterocyclic rings (H) and one monocyclic hydrocarbon ring having 5 members or 6 members are fused; and a heterocyclic group in which one heterocyclic ring (H) and two monocyclic hydrocarbon rings having 5 members or 6 members are fused. Specific examples of the heterocyclic group having at least 5 members and no greater than 14 members include a piperidinyl group, a piperazinyl group, a morpholinyl group, a thiophenyl group, a furanyl group, a pyrrolyl group, an imidazolyl group, a pyrazolyl group, an isothiazolyl group, an isoxazolyl group, an oxazolyl group, a thiazolyl group, a furazanyl group, a pyranyl group, a pyridyl group, a pyridazinyl group, a pyrimidinyl group, a pyrazinyl group, an indolyl group, a 1H-indazolyl group, an isoindolyl group, a chromenyl group, a quinolinyl group, an isoquinolinyl group, a purinyl group, a pteridinyl group, a triazolyl group, a tetrazolyl group, a 4H-quinolizinyl group, a naphthyridinyl, a benzofurany group, a 1,3-benzodioxolyl group, a benzoxazolyl group, a benzothiazolyl group, a benzimidazolyl group, a carbazolyl group, a phenanthridinyl group, an acridinyl group, a phenazinyl group, and a phenanthrolinyl group.

First Embodiment: Bis-Butadiene Derivative

A bis-butadiene derivative according to a first embodiment of the present disclosure is represented by general formula (1) shown below. The bis-butadiene derivative represented by the following general formula (1) may be also referred to below as a bis-butadiene derivative (1).

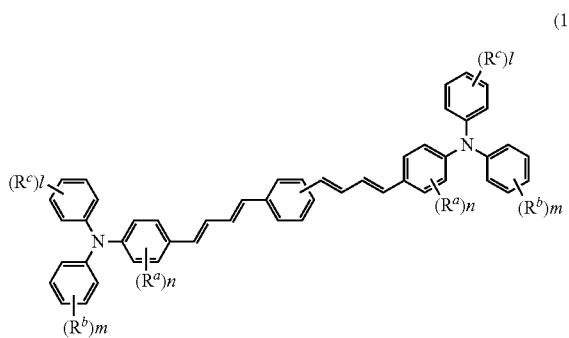

(1)

In general formula (1), $R^a$, $R^b$, and $R^c$ each represent, independently of one another, an alkyl group having a carbon number of at least 1 and no greater than 8 or an alkoxy group having a carbon number of at least 1 and no greater than 8. l and m each represent, independently of one another, an integer of at least 0 and no greater than 5. n represents an integer of at least 0 and no greater than 4. Plural chemical groups $R^a$ may be the same as or different from each other. Plural chemical groups $R^b$ may be the same as or different from each other. Plural chemical groups $R^c$ may be the same as or different from each other. Plural indices l may be the same as or different from each other. Plural indices m may be the same as or different from each other. Plural indices n may be the same as or different from each other.

The bis-butadiene derivative (1) can be used as a charge transport material (particularly, a hole transport material) in formation of a photosensitive layer of an electrophotographic photosensitive member (also referred to below as a photosensitive member). Use of the bis-butadiene derivative (1) as a charge transport material of a photosensitive member can improve sensitivity characteristics of the photosensitive member. Presumably, the reason therefor is as follows.

The bis-butadiene derivative (1) has a π conjugated system having relatively large spatial spread. Therefore, the bis-butadiene derivative (1) tends to have excellent acceptability of a carrier (holes). The bis-butadiene derivative (1) has a relatively large π conjugated system. Therefore, a travel distance of a carrier (holes) in a molecule is relatively long while a travel distance of the carrier (holes) between molecules is relatively short. For the reason as above, the bis-butadiene derivative (1) tends to have excellent transportability of the carrier (holes). The bis-butadiene derivative (1) tends to have excellent acceptability and transportability of the charrier (holes) as described above. Accordingly, use of the bis-butadiene derivative (1) can be thought to improve sensitivity characteristics of a photosensitive member.

Note that it is difficult to synthesize the bis-butadiene derivative (1) by any known synthesis method. For example, a compound represented by chemical formula (h-3) shown above, which is a known charge transport material, can be obtained through a reaction between tetraethyl o-xylylenediphosphonate and 4-(di-p-tolylamino)benzaldehyde. However, the bis-butadiene derivative (1) cannot be obtained through such a known synthetic route in view of percentage yield and the like. By contrast, the present inventors have found that use of a synthetic rout including a reaction represented by chemical equation (P) described later can achieve efficient synthesis of the bis-butadiene derivative (1) to arrive at the present disclosure.

In general formula (1), an alkyl group having a carbon number of at least 1 and no greater than 8 that may be represented by $R^a$, $R^b$, or $R^c$ is preferably an alkyl group having a carbon number of at least 1 and no greater than 6, more preferably an alkyl group having a carbon number of at least 1 and no greater than 3, and further preferably a methyl group.

In general formula (1), an alkoxy group having a carbon number of at least 1 and no greater than 8 that may be represented by $R^a$, $R^b$, or $R^c$ is preferably an alkoxy group having a carbon number of at least 1 and no greater than 6, more preferably an alkoxy group having a carbon number of at least 1 and no greater than 3, and further preferably a methoxy group.

In general formula (1), preferably, m and l each represent, independently of one another, an integer of at least 0 and no greater than 2. When either one of m and l represents 0, the other preferably represents an integer of at least 1 and no greater than 5 and more preferably 1 or 2.

In general formula (1), n preferably represents an integer of at least 0 and no greater than 2, and more preferably represents 0.

In general formula (1), preferably, $R^b$ and $R^c$ each represent, independently of one another, an alkyl group having a carbon number of at least 1 and no greater than 3 or an alkoxy group having a carbon number of at least 1 and no greater than 3. Preferably, l and m each represent, independently of one another, an integer of at least 0 and no greater than 2. Preferably, n represents 0.

In general formula (1), plural chemical groups $R^a$ are preferably the same as each other. In general formula (1), plural chemical groups $R^b$ are preferably the same as each other. In general formula (1), plural chemical groups $R^c$ are preferably the same as each other. In general formula (1), plural indices l are preferably the same as each other. In general formula (1), plural indices m are preferably the same as each other. In general formula (1), plural indices n are preferably the same as each other.

Examples of the bis-butadiene derivative (1) include compounds represented by general formulas (1-a), (1-b), and (1-c) shown below. The compounds represented by general formulas (1-a) and (1-b) are preferable among the compounds represented by general formulas (1-a), (1-b), and (1-c).

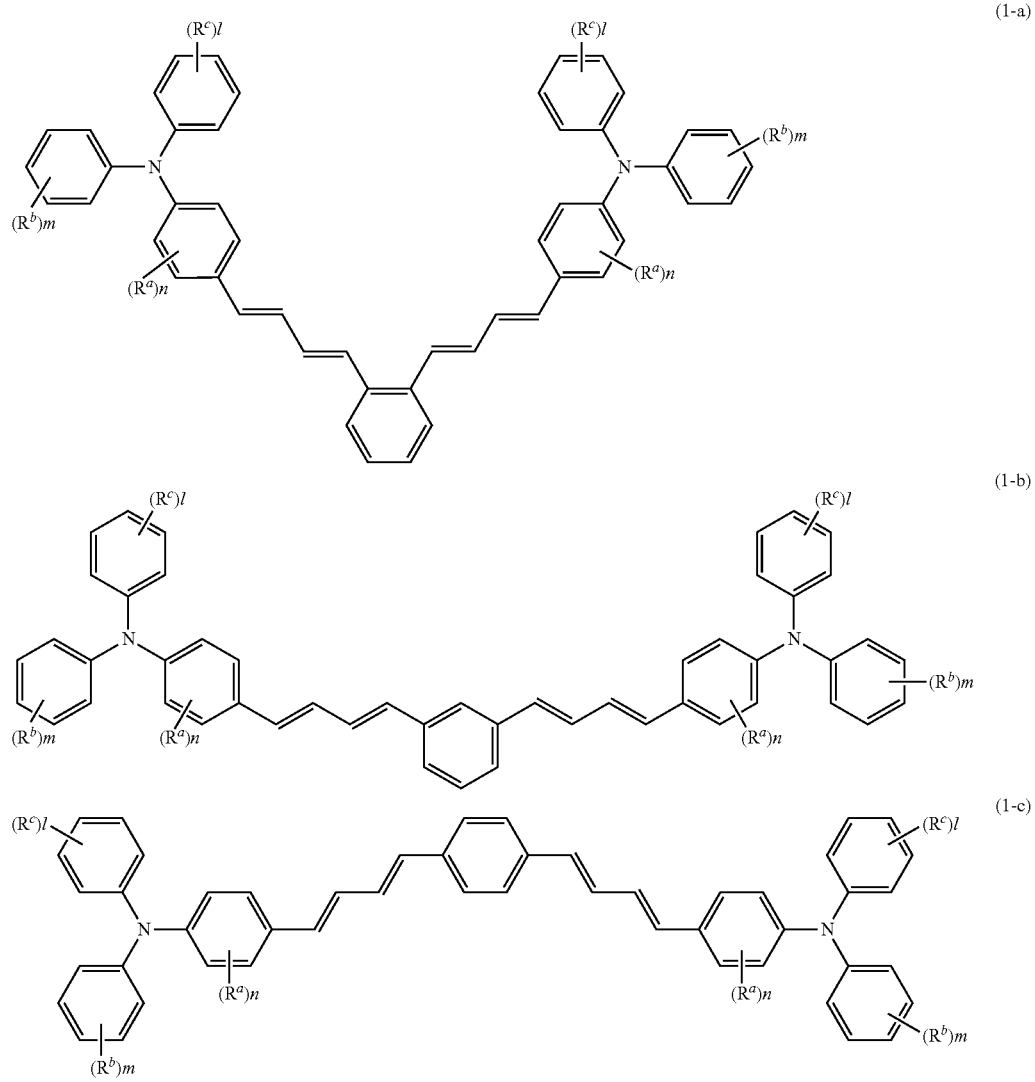

(1-a)

(1-b)

(1-c)

In general formulas (1-a), (1-b), and (1-c), $R^a$, $R^b$, $R^c$, l, m, and n are respectively the same as defined for $R^a$, $R^b$, $R^c$, l, m, and n in general formula (1).

Compounds represented by chemical formulas (HTM-1), (HTM-2), (HTM-3), (HTM-4), and (HTM-5) shown below (also referred to below as bis-butadiene derivatives (HTM-1), (HTM-2), (HTM-3), (HTM-4), and (HTM-5), respectively) are preferable as the bis-butadiene derivative (1).

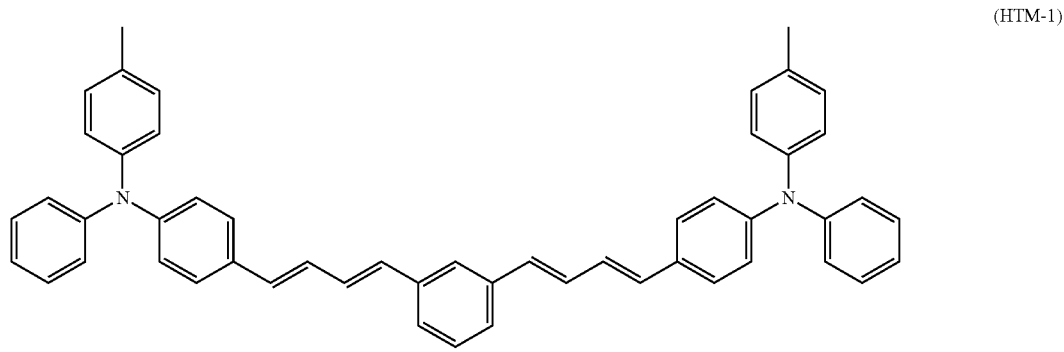

(HTM-1)

(HTM-2)
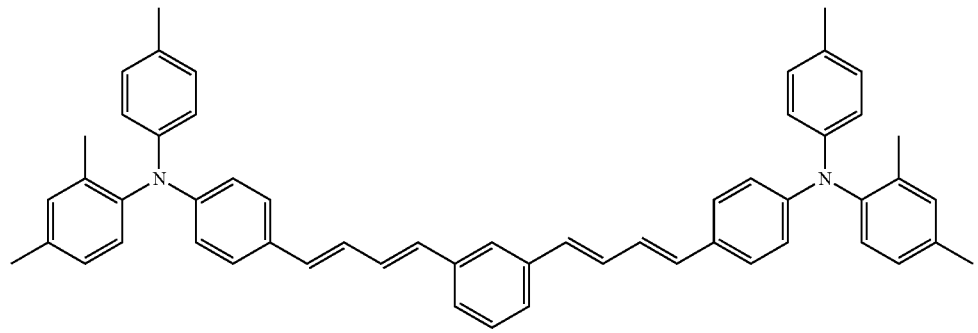
(HTM-3)
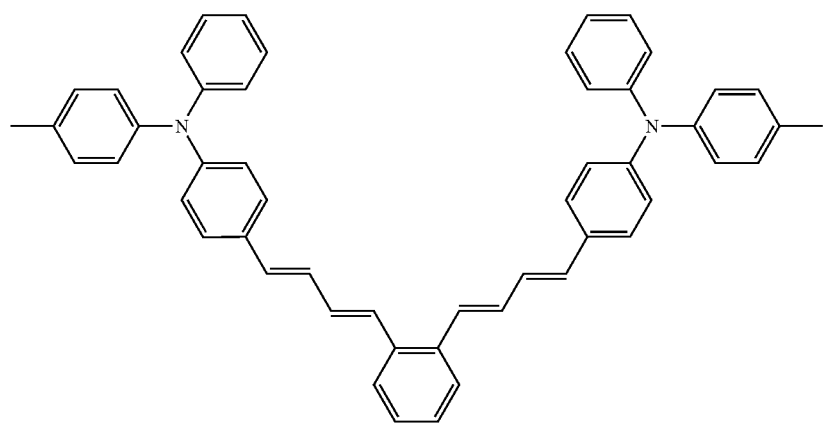
(HTM-4)
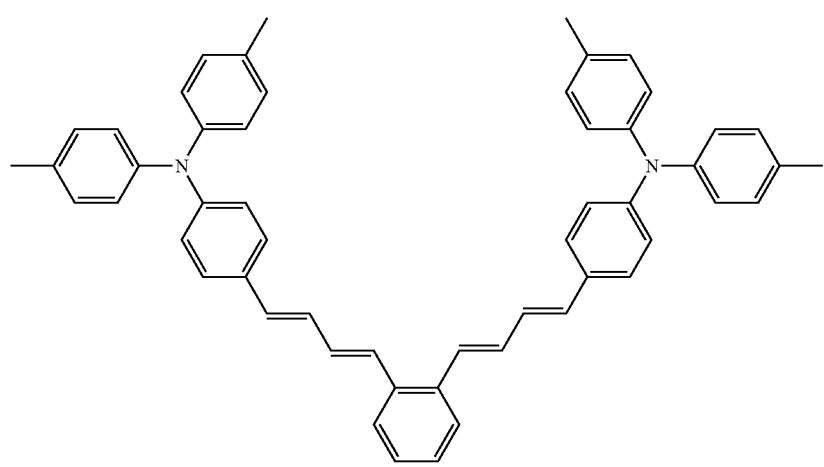

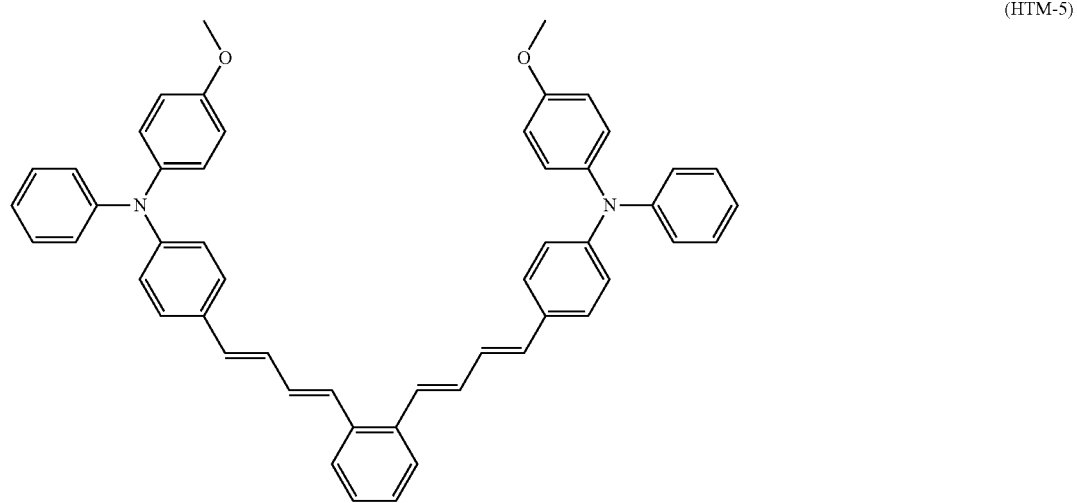 [SMILES: COc1ccc(N(c2ccccc2)c2ccc(/C=C/C=C/c3ccccc3/C=C/C=C/c3ccc(N(c4ccccc4)c4ccc(OC)cc4)cc3)cc2)cc1]

(HTM-5)

Second Embodiment: Production Method of Bis-Butadiene Derivative (1)

A production method of the bis-butadiene derivative (1) according to a second embodiment of the present disclosure includes carrying out a reaction represented by chemical equation (P) shown below (also referred to below as a reaction (P)). Hereinafter, compounds represented by general formulas (10) and (11) in chemical equation (P) may be referred to below as a bis-butadiene halide compound (10) and a diphenylamine compound (11), respectively. According to the production method of the bis-butadiene derivative (1) according to the second embodiment of the present disclosure, the bis-butadiene derivative (1) can be produced efficiently through use of a synthetic route using the bis-butadiene halide compound (10) as a raw material compound. Specifically, through use of the synthetic route, the bis-butadiene derivative (1) can be synthesized at a significantly high percentage yield and the synthesized bis-butadiene derivative (1) can be purified easily, with a result that the bis-butadiene derivative (1) can be produced at low cost.

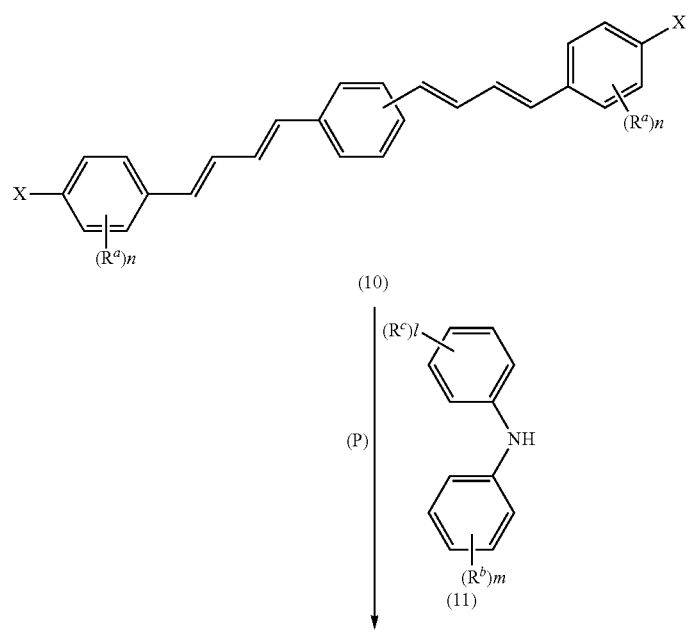

-continued

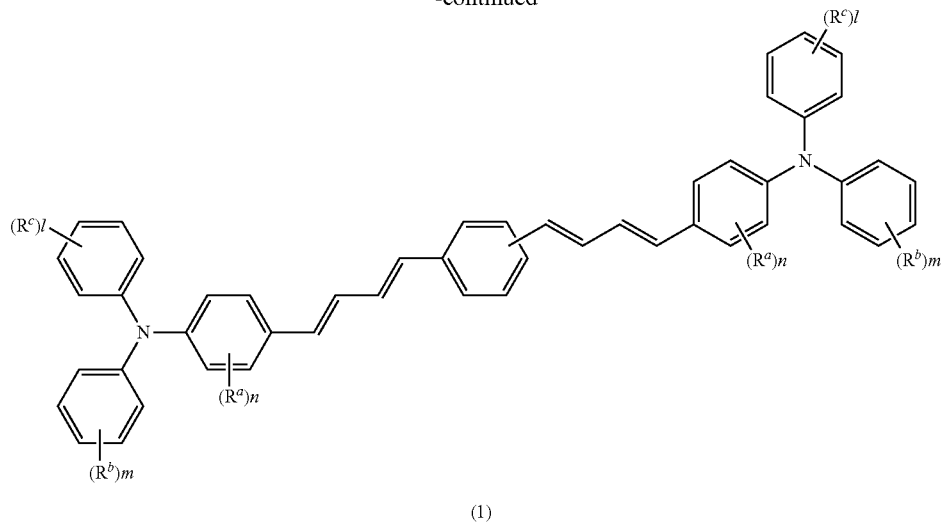

(1)

In chemical equation (P), $R^a$, $R^b$, $R^c$, l, m, and n are respectively the same as defined for $R^a$, $R^b$, $R^c$, l, m, and n in general formula (1). X represents a halogen atom. Plural atoms X may be the same as or different from each other.

In reaction (P), 1 mole equivalent of the bis-butadiene halide compound (10) and 2 mole equivalents of the diphenylamine compound (11) are caused to react together to give 1 mole equivalent of the bis-butadiene derivative (1). A palladium compound is preferably used as a catalyst in reaction (P). Use of a palladium compound as a catalyst tends to reduce activation energy in reaction (P). Therefore, high percentage yield of the bis-butadiene derivative (1) is thought to be attained.

Examples of the palladium compound include tetravalent palladium compounds, divalent palladium compounds, and other palladium compounds. Examples of tetravalent palladium compounds include sodium hexachloropalladate(IV) tetrahydrate and potassium hexachloropalladate(IV) tetrahydrate. Examples of divalent palladium compounds include palladium(II) chloride, palladium(II) bromide, palladium(II) acetate, palladium(II) acetylacetate, dichlorobis(benzonitrile)palladium(II), dichlorobis(triphenylphosphine)palladium(II), dichlorotetramine palladium(II), and dichloro(cyclootra-1,5-diene)palladium(II). Examples of the other palladium compounds include tris(dibenzylideneacetone)dipalladium(0), tris(dibenzylideneacetone)dipalladium(0) chloroform complex, and tetrakis(triphenylphosphine)palladium(0). Any one of the palladium compounds may be used independently, any two or more of the palladium compounds may be used in combination. Palladium(II) acetate is preferable as the palladium compound.

In a situation in which a palladium compound is used as a catalyst in reaction (P), the amount of the palladium compound is preferably at least 0.0005 mol and no greater than 20 mol relative to 1 mol of the bis-butadiene halide compound (10), and more preferably at least 0.001 mol and no greater than 1 mol.

In a situation in which a palladium compound is used as a catalyst, a ligand may be added in addition in order to further improve reactivity of reaction (P). Examples of the ligand that can be used include tricyclohexylphosphine, triphenylphosphine, methyldiphenylphosphine, trifurylphosphine, tri(o-tolyl)phosphine, dicyclohexylphenylphosphine, 2-dicyclohexylphosphino-2',4',6'-triisopropylbiphenyl, tri(t-butyl)phosphine, 2,2'-bis(diphenylphosphino)-1,1'-binaphthyl, and 2,2'-bis[(diphenylphosphino)diphenyl]ether. Any one of the ligands may be used independently, or any two or more of the ligands may be used in combination. As the ligand, 2-dicyclohexylphosphino-2',4',6'-triisopropylbiphenyl is preferable.

In a situation in which a ligand is added in reaction (P), the amount of the ligand is preferably at least 0.0005 mol and no greater than 20 mol relative to 1 mol of the bis-butadiene halide compound (10), and more preferably at least 0.001 mol and no greater than 1 mol.

Reaction (P) is preferably carried out in the presence of a base. As a result of reaction (P) being carried out in the presence of a base, a hydrogen halide generated in a reaction system (for example, hydrogen chloride) is thought to be quickly neutralized to enhance catalyst activity. Thus, percentage yield of the bis-butadiene derivative (1) is thought to be increased. The base may be an inorganic base or an organic base. Examples of the organic base include alkali metal alkoxides (specific examples include sodium methoxide, sodium ethoxide, potassium methoxide, potassium ethoxide, lithium tert-butoxide, sodium tert-butoxide, and potassium tert-butoxide). Of the alkali metal alkoxides listed above, sodium tert-butoxide is preferable. Examples of the inorganic bases include tripotassium phosphate and cesium fluoride.

In a situation in which a base and a palladium compound as a catalyst are used in reaction (P), the amount of the base is adjusted as appropriate according to the amount of the palladium compound. Specifically, in a situation in which at least 0.0005 mol and no greater than 20 mol of the palladium compound is added relative to 1 mol of the bis-butadiene halide compound (1), the amount of the base is preferably at least 1 mol and no greater than 10 mol relative to 1 mol of the bis-butadiene halide compound (10), and more preferably at least 1 and no greater than 5 mol.

Reaction (P) may be carried out in a solvent. Examples of the solvent that may be used include xylenes (specific examples include mixed xylenes), toluene, tetrahydrofuran, and dimethyl formamide. Xylenes are preferable as the solvent, and a mixed xylene is more preferable.

The amount of the diphenylamine compound (11) in reaction (P) is preferably at least 0.5 mol and no greater than 10 mol relative to 1 mol of the bis-butadiene halide compound (10), and more preferably at least 1.5 mol and no greater than 4 mol.

Reaction (P) is preferably carried out at a reaction temperature of 120° C. or higher and 180° C. or lower. The reaction time of reaction (P) is preferably 1 hour or longer and 10 hours or shorter.

The bis-butadiene derivative (1) as a product of reaction (P) may be purified as necessary. Examples of purification methods include known methods (for example, filtering, silica gel chromatography, and crystallization).

Third Embodiment: Electrophotographic Photosensitive Member

A third embodiment of the present disclosure relates to a photosensitive member. The photosensitive member according to the third embodiment includes a conductive substrate and a photosensitive layer located either directly or indirectly on the conductive substrate. Examples of the photosensitive member include a single-layer electrophotographic photosensitive member (also referred to below as a single-layer photosensitive member) and a multi-layer electrophotographic photosensitive member (also referred to below as a multi-layer photosensitive member).

[Single-Layer Photosensitive Member]

Figure 2:
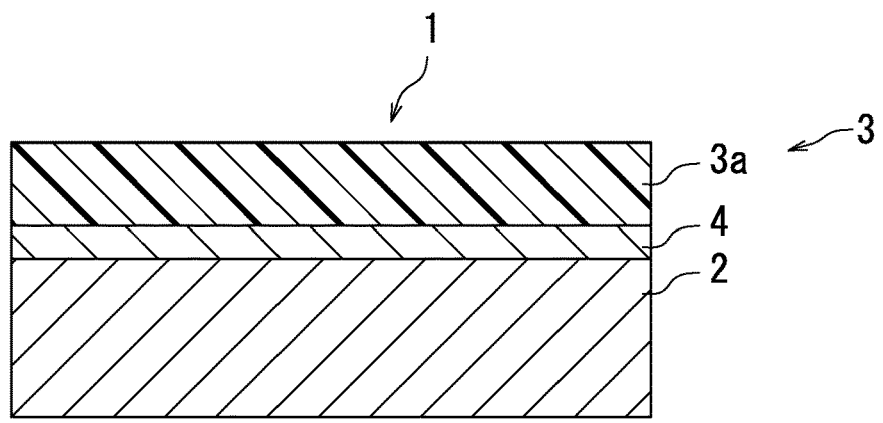
FIG. 2 is a cross-sectional view of another example of the electrophotographic photosensitive member according to the third embodiment of the present disclosure.
Figure 3:
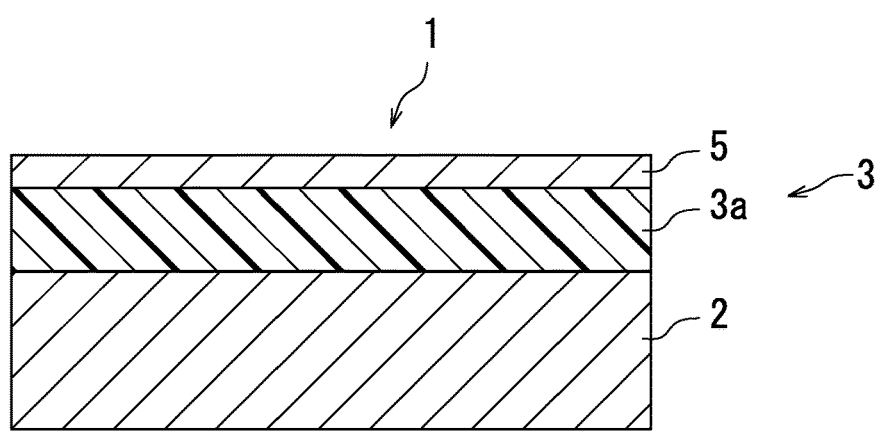
FIG. 3 is a cross-sectional view of another example of the electrophotographic photosensitive member according to the third embodiment of the present disclosure.

The following describes a structure of the single-layer photosensitive member with reference to FIGS. 1 to 3. FIGS. 1 to 3 are each a schematic cross-sectional view of an example of a photosensitive member 1 according to the third embodiment.

FIG. 1 illustrates a single-layer photosensitive member as the photosensitive member 1. As illustrated in FIG. 1, the single-layer photosensitive member includes for example a conductive substrate 2 and a photosensitive layer 3. The single-layer photosensitive member includes a single-layer photosensitive layer 3a as the photosensitive layer 3. The single-layer photosensitive layer 3a is the photosensitive layer 3 of one layer. As illustrated in FIG. 1, the photosensitive layer 3 may be disposed directly on the conductive substrate 2.

As illustrated in FIG. 2, the single-layer photosensitive member may include the conductive substrate 2, the single-layer photosensitive layer 3a, and an intermediate layer 4 (undercoat layer). The intermediate layer 4 is disposed between the conductive substrate 2 and the single-layer photosensitive layer 3a. As illustrated in FIG. 2, the photosensitive layer 3 may be disposed indirectly on the conductive substrate 2 with the intermediate layer 4 therebetween. Alternatively or additionally, as illustrated in FIG. 3, a protective layer 5 may be disposed on the single-layer photosensitive layer 3a.

No particular limitations are placed on the thickness of the single-layer photosensitive layer 3a so long as the thicknesses thereof are sufficient to enable the single-layer photosensitive layer 3a to implement its function. The single-layer photosensitive layer 3a preferably has a thickness of at least 5 μm and no greater than 100 μm, and more preferably at least 10 μm and no greater than 50 μm.

[Multi-Layer Photosensitive Member]

Figure 4:
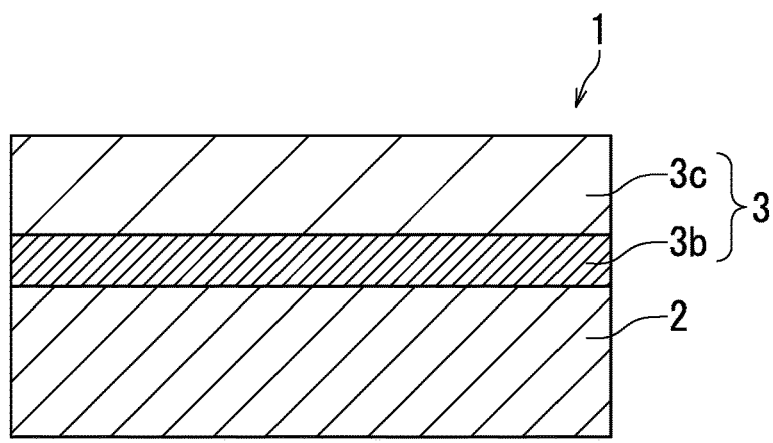
FIG. 4 is a cross-sectional view of another example of the electrophotographic photosensitive member according to the third embodiment of the present disclosure.
Figure 5:
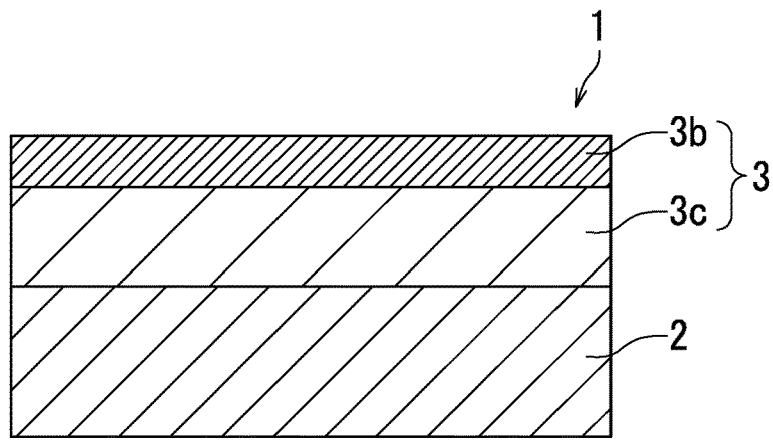
FIG. 5 is a cross-sectional view of another example of the electrophotographic photosensitive member according to the third embodiment of the present disclosure.
Figure 6:
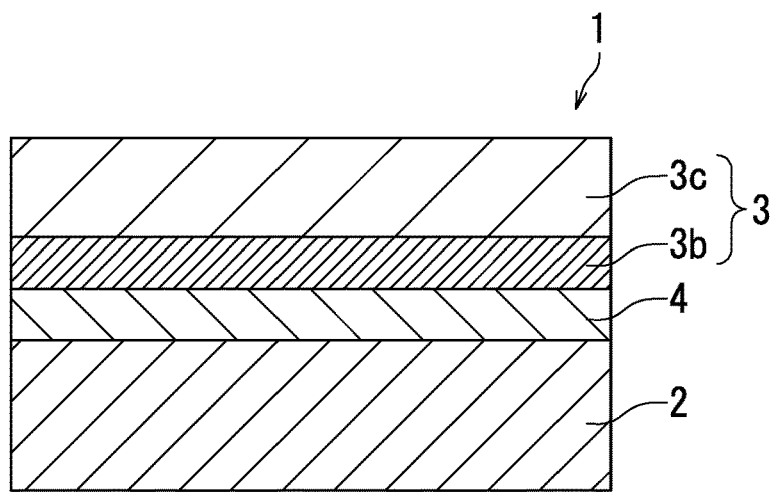
FIG. 6 is a cross-sectional view of another example of the electrophotographic photosensitive member according to the third embodiment of the present disclosure.

A multi-layer photosensitive member includes as a photosensitive layer, a charge generating layer and a charge transport layer. The following describes a structure of the multi-layer photosensitive member with reference to FIGS. 4 to 6. FIGS. 4 to 6 are each a schematic cross-sectional view of another example of the photosensitive member 1 according to the third embodiment.

FIG. 4, illustrates a multi-layer photosensitive member as the photosensitive member 1. As illustrated in FIG. 4, the multi-layer photosensitive member includes for example a conductive substrate 2 and a photosensitive layer 3. The photosensitive layer 3 includes a charge generating layer 3b and a charge transport layer 3c. In order to improve abrasion resistance of the multi-layer photosensitive member, it is preferable that the charge generating layer 3b is disposed on the conductive substrate 2 and the charge transport layer 3c is disposed on the charge generating layer 3b as illustrated in FIG. 4. As illustrated in FIG. 5, it is possible that the charge transport layer 3c is disposed on the conductive substrate 2 and the charge generating layer 3b is disposed on the charge transport layer 3c in the multi-layer photosensitive member.

As illustrated in FIG. 6, the multi-layer photosensitive member may include for example the conductive substrate 2, the photosensitive layer 3, and an intermediate layer 4 (undercoat layer). The intermediate layer 4 is disposed between the conductive substrate 2 and the photosensitive layer 3. Alternatively or additionally, a protective layer 5 (see FIG. 3) may be disposed on the photosensitive layer 3.

No particular limitations are placed on the respective thicknesses of the charge generating layer 3b and the charge transport layer 3c so long as the thicknesses thereof are sufficient to enable the charge generating layer 3b and the charge transport layer 3c to implement their respective functions. The charge generating layer 3b preferably has a thickness of at least 0.01 μm and no greater than 5 μm, and more preferably at least 0.1 μm and no greater than 3 μm. The charge transport layer 3c preferably has a thickness of at least 2 μm and no greater than 100 μm, and more preferably at least 5 μm and no greater than 50 μm.

The photosensitive layer 3 of the photosensitive member 1 according to the third embodiment contains at least a charge generating material, a charge transport material, and a binder resin. The charge transport material includes the bis-butadiene derivative (1) according to the first embodiment. The single-layer photosensitive layer 3a of the single-layer photosensitive member contains for example a charge generating material, a charge transport material, and a binder resin. The charge generating layer 3b of the multi-layer photosensitive member contains for example a charge generating material and a binder resin for charge generating layer formation (also referred to below as a base resin). The charge transport layer 3c contains for example a charge transport material and a binder resin. The single-layer photosensitive layer 3a, the charge generating layer 3b, and the charge transport layer 3c may each further contain an additive. As a result of the photosensitive layer 3 containing the bis-butadiene derivative (1) as a charge transport material, the photosensitive member 1 according to the third embodiment is excellent in sensitivity characteristics.

[Conductive Substrate]

It is only required for the conductive substrate 2 that at least a surface portion thereof be made from a material having conductivity (also referred to below as a conductive material). An example of the conductive substrate 2 is a conductive substrate made from a conductive material. Another example of the conductive substrate 2 is a conductive substrate covered with a conductive material. Examples of conductive materials include aluminum, iron, copper, tin, platinum, silver, vanadium, molybdenum, chromium, cadmium, titanium, nickel, palladium, and indium. Any one of the conductive materials listed above may be used independently, or any two or more of the conductive materials listed above may be used in combination. Examples of combinations of two or more conductive materials include alloys (specific examples include aluminum alloys, stainless steel, and brass). Of the conductive materials, aluminum and aluminum alloys are preferable in terms of favorable charge mobility from the photosensitive layer 3 to the conductive substrate 2. Alternatively, the conductive substrate 2 may include an oxide film of any of the conductive materials listed above on a surface thereof.

The shape of the conductive substrate 2 is selected as appropriate according to a configuration of an image forming apparatus for which the conductive substrate 2 is used. Examples of the shape of the conductive substrate 2 include a sheet-like shape and a drum-like shape. The thickness of the conductive substrate 2 is selected as appropriate according to the shape of the conductive substrate 2.

(Charge Generating Material)

In a situation in which the photosensitive member 1 is a single-layer photosensitive member, the single-layer photosensitive layer 3a contains a charge generating material. In a situation in which the photosensitive member 1 is a multi-layer photosensitive member, the charge generating layer 3b contains a charge generating material.

Examples of the charge generating material include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. Any one of the charge generating materials may be used independently, or any two or more of the charge generating materials may be used in combination.

Examples of the phthalocyanine-based pigments include metal phthalocyanine pigments and metal-free phthalocyanine pigments. Examples of the metal phthalocyanine pigments include a hydroxygallium phthalocyanine pigment, a chlorogallium phthalocyanine pigment, and a titanyl phthalocyanine pigment represented by chemical formula (CGM-A) shown below. A metal-free phthalocyanine pigment is represented by chemical formula (CGM-B) shown below. No particular limitations are placed on the crystal structures (for example, X-form, α-form, β-form, Y-form, V-form, and II-form) of the phthalocyanine-based pigments, and phthalocyanine-based pigments having various crystal structures are used.

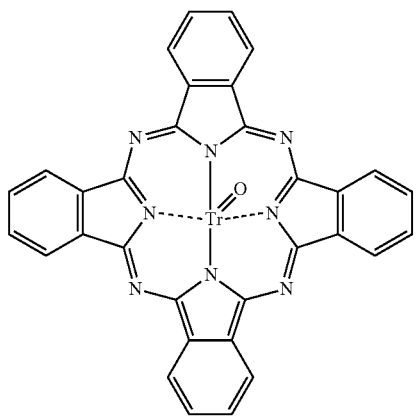

(CGM-A)

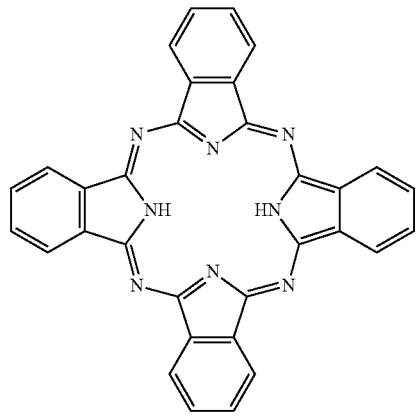

(CGM-B)

An example of crystalline metal-free phthalocyanine is metal-free phthalocyanine having an X-form crystal structure (also referred to below as X-form metal-free phthalocyanine). Examples of crystalline titanyl phthalocyanine pigments include titanyl phthalocyanine pigments having α-form crystal structure, β-form crystal structure, and Y-form crystal structure (also referred to below as α-form titanyl phthalocyanine crystal, β-form titanyl phthalocyanine crystal, and Y-form titanyl phthalocyanine crystal, respectively). Examples of crystalline hydroxygallium phthalocyanine pigments include a hydroxygallium phthalocyanine pigment having a V-form crystal structure. Examples of crystalline chlorogallium phthalocyanine include a chlorogallium phthalocyanine pigment having a II-form crystal structure.

For example, a photosensitive member having sensitivity in a wavelength range of at least 700 nm is preferably used in digital optical image forming apparatuses. Examples of digital optical image forming apparatuses include laser beam printers and facsimile machines that use light sources such as a semiconductor laser. In view of high quantum yield in a wavelength range of at least 700 nm, phthalocyanine-based pigments are preferable as the charge generating material, titanyl phthalocyanine pigments are more preferable, and a Y-form titanyl phthalocyanine pigment is further preferable.

Y-form crystalline titanyl phthalocyanine exhibits a main peak for example at a Bragg angle ($2\theta \pm 0.2°$) of 27.2° in a CuKα characteristic X-ray diffraction spectrum. The term main peak refers to a peak having the largest or second largest intensity within a range of Bragg angles ($2\theta \pm 0.2°$) from 3° to 40° in a CuKα characteristic X-ray diffraction spectrum.

(Method for Measuring CuKα Characteristic X-ray Diffraction Spectrum) The following describes an example of a method for measuring a CuKα characteristic X-ray diffraction spectrum. A sample (a Y-form titanyl phthalocyanine pigment) is loaded into a sample holder of an X-ray diffraction spectrometer (for example, "RINT (registered Japanese trademark) 1100", product of Rigaku Corporation), and an X-ray diffraction spectrum is measured using a Cu X-ray tube under conditions of a tube voltage of 40 kV, a tube current of 30 mA, and an X-ray characteristic of CuKα having a wavelength of 1.542 Å. The measurement range ($2\theta$) is for example from 3° to 40° (start angle: 3°, stop angle: 40°), and the scanning speed is for example 10°/minute.

In a situation in which the photosensitive member 1 is a multi-layer photosensitive member, the amount of the charge generating material in the charge generating layer 3b is preferably at least 5 parts by mass and no greater than 1,000 parts by mass relative to 100 parts by mass of the base resin, and more preferably at least 30 parts by mass and no greater than 500 parts by mass.

(Charge Transport Material)

The photosensitive layer 3 contains a charge transport material. Examples of the charge transport material include an electron transport material and a hole transport material. The charge transport material includes the above-described bis-butadiene derivative (1). The bis-butadiene derivative (1) usually functions as a hole transport material in the photosensitive layer 3. In the single-layer photosensitive member, the bis-butadiene derivative (1) is contained in the single-layer photosensitive layer 3a. In the multi-layer photosensitive member, the bis-butadiene derivative (1) is contained in the charge transport layer 3c.

In a situation in which the photosensitive member 1 is a multi-layer photosensitive member, the amount of the bis-butadiene derivative (1) in the charge transport layer 3c is preferably at least 10 parts by mass and no greater than 200 parts by mass relative to 100 parts by mass of the binder resin, and more preferably at least 20 parts by mass and no greater than 100 parts by mass.

The photosensitive layer 3 may further contain a hole transport material that is not the bis-butadiene derivative (1) (also referred to below as an additional hole transport material) in addition to the bis-butadiene derivative (1). Examples of the additional hole transport material include triphenylamine derivatives, diamine derivatives (for example, an N,N,N',N'-tetraphenylbenzidine derivative, an N,N,N',N'-tetraphenylphenylenediamine derivative, an N,N,N',N'-tetraphenylnaphtylenediamine derivative, an N,N,N',N'-tetraphenylphenanthrylenediamine derivative, and a di(aminophenylethenyl)benzene derivative), oxadiazole-based compounds (for example, 2,5-di(4-methylaminophenyl)-1,3,4-oxadiazole), styryl-based compounds (for example, 9-(4-diethylaminostyryl)anthracene), carbazole-based compounds (for example, polyvinyl carbazole), organic polysilane compounds, pyrazoline-based compounds (for example, 1-phenyl-3-(p-dimethylaminophenyl) pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Any one of the additional hole transport materials listed above may be used independently, or any two or more of the additional hole transport materials listed above may be used in combination.

The photosensitive layer 3 may contain only the bis-butadiene derivative (1) as a hole transport material. The mass of the bis-butadiene derivative (1) relative to a total mass of the hole transport material is preferably at least 80% by mass, more preferably at least 90% by mass, and particularly preferably 100% by mass.

The single-layer photosensitive layer 3a of the single-layer photosensitive member may further contain an electron transport material as a charge transport material.

Examples of the electron transport material include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of quinone-based compounds include diphenoquinone-based compounds, azoquinone-based compounds, anthraquinone-based compounds, naphthoquinone-based compounds, nitroanthraquinone-based compounds, and dinitroanthraquinone-based compounds. Any one of the electron transport materials may be used independently, or any two or more of the electron transport materials may be used in combination.

Compounds represented by general formulas (E-1) to (E-4) shown below are preferable as an electron transport material.

The following describes an electron transport material represented by general formula (E-1) shown below.

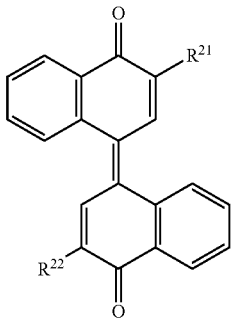

(E-1)

In general formula (E-1), $R^{21}$ and $R^{22}$ each represent, independently of one another, an alkyl group having a carbon number of at least 1 and no greater than 6, an alkoxy group having a carbon number of at least 1 and no greater than 6, an aryl group having a carbon number of at least 6 and no greater than 14, or an aralkyl group having a carbon number of at least 7 and no greater than 20.

In general formula (E-1), preferably, $R^{21}$ and $R^{22}$ each represent, independently of one another, an alkyl group having a carbon number of at least 1 and no greater than 6. An alkyl group having a carbon number of at least 1 and no greater than 6 that may be represented by $R^{21}$ or $R^{22}$ in general formula (E-1) is preferably an alkyl group having a carbon number of at least 1 and no greater than 5, and more preferably a 1,1-dimethylpropyl group.

A compound represented by chemical formula (ETM-1) (also referred to below as a compound (ETM-1)) shown below is preferable as the compound represented by general formula (E-1).

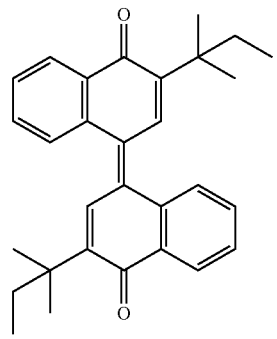

(ETM-1)

The following describes a compound represented by general formula (E-2) shown below.

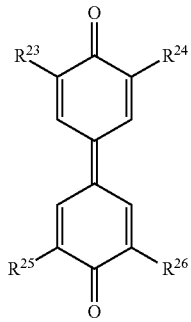

(E-2)

In general formula (E-2), $R^{23}$, $R^{24}$, $R^{25}$, and $R^{26}$ each represent, independently of one another, an alkyl group having a carbon number of at least 1 and no greater than 6.

In general formula (E-2), preferably, $R^{23}$, $R^{24}$, $R^{25}$, and $R^{26}$ each represent, independently of one another, an alkyl group having a carbon number of at least 1 and no greater than 4.

Compounds represented by chemical formulas (ETM-2) and (ETM-3) (also referred to below as compounds (ETM-2) and (ETM-3), respectively) shown below are preferable as the compound represented by general formula (E-2).

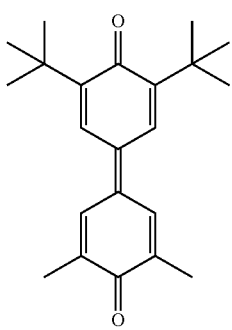

(ETM-2)

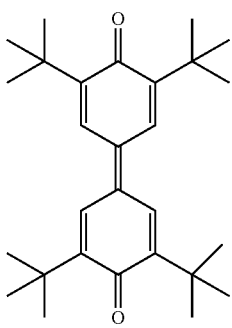

(ETM-3)

The following describes a compound represented by general formula (E-3) shown below.

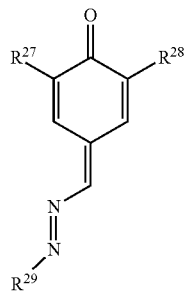

(E-3)

In general formula (E-3), $R^{27}$ and $R^{28}$ each represent, independently of one another, an alkyl group having a carbon number of at least 1 and no greater than 6. $R^{29}$ represents an aryl group having a carbon number of at least 6 and no greater than 14 and optionally substituted by a halogen atom.

In general formula (E-3), preferably, $R^{27}$ and $R^{28}$ each represent, independently of one another, an alkyl group having a carbon number of at least 1 and no greater than 4. In general formula (E-3), $R^{29}$ preferably represents a phenyl group substituted by a halogen atom, and more preferably represents a phenyl group substituted by a chlorine atom.

A compound represented by chemical formula (ETM-4) (also referred to below as a compound (ETM-4)) shown below is preferable as the compound represented by general formula (E-3).

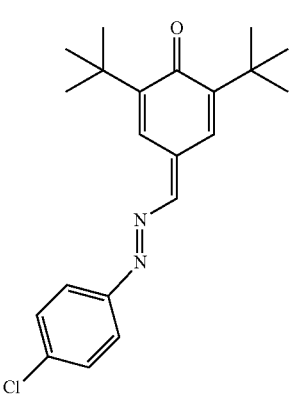

(ETM-4)

The following describes a compound represented by general formula (E-4) shown below.

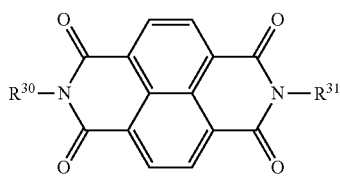

(E-4)

In general formula (E-4), $R^{30}$ and $R^{31}$ each represent, independently of one another, an aryl group having a carbon number of at least 6 and no greater than 14 and optionally substituted by an alkyl group having a carbon number of at least 1 and no greater than 4.

In general formula (E-4), preferably, $R^{30}$ and $R^{31}$ each represent, independently of one another, a phenyl group substituted by an alkyl group having a carbon number of at least 1 and no greater than 4, and more preferably a phenyl group in which two hydrogen atoms are each replaced by an alkyl group having a carbon number of at least 1 and no greater than 4.

A compound represented by chemical formula (ETM-5) (also referred to below as a compound (ETM-5)) shown below is preferable as the compound represented by general formula (E-4).

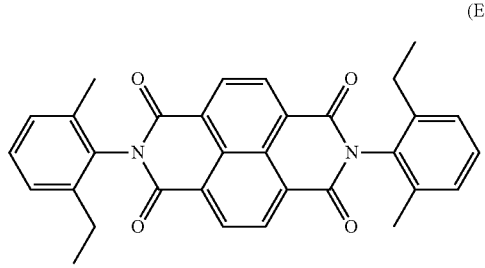

(ETM-5)

The charge transport layer $3c$ of the multi-layer photosensitive member may further contain any of the above electron transport materials. In a case where the charge transport layer $3c$ of the multi-layer photosensitive member further contains any of the above electron transport materials, the contained electron transport material functions as an electron acceptor compound in the charge transport layer $3c$. Preferable electron acceptor compounds are the compounds represented by general formulas (E-1) to (E-4), and more preferable electron acceptor compounds are the compounds (ETM-1), (ETM-2), (ETM-3), (ETM-4), and (ETM-5).

In a situation in which the photosensitive member 1 is a multi-layer photosensitive member, the amount of the electron acceptor compound in the charge transport layer $3c$ is preferably at least 0.1 parts by mass and no greater than 20 parts by mass relative to 100 parts by mass of the binder resin, more preferably at least 0.5 parts by mass and no greater than 5 parts by mass, and particularly preferably at least 1 part by mass and no greater than 3 parts by mass.

(Binder Resin)

Examples of the binder resin include thermoplastic resins, thermosetting resins, and photocurable resins. Examples of thermoplastic resins include polycarbonate resins, polyarylate resins, styrene-butadiene copolymers, styrene-acrylonitrile copolymers, styrene-maleate copolymers, acrylic acid-based resins, styrene-acrylate copolymers, polyethylene resins, ethylene-vinyl acetate copolymers, chlorinated polyethylene resins, polyvinyl chloride resins, polypropylene resins, ionomer resins, vinyl chloride-vinyl acetate copolymers, alkyd resins, polyamide resins, urethane resins, polysulfone resins, diallyl phthalate resins, ketone resins, polyvinyl butyral resins, polyester resins, and polyether resins. Examples of thermosetting resins include silicone resins, epoxy resins, phenolic resins, urea resins, and melamine resins. Examples of photocurable resins include acrylic acid adducts of epoxy compounds and acrylic acid adducts of urethane compounds. The photosensitive layer 3 may contain any one of the binder resins listed above independently or contain any two or more of the binder resins listed above in combination.

Of the resins listed above, polyarylate resins and polycarbonate resins are preferable and a polyarylate resin including a repeating unit represented by general formula (r-1) shown below and a polycarbonate resin including a repeating unit represented by general formula (r-2) shown below are more preferable.

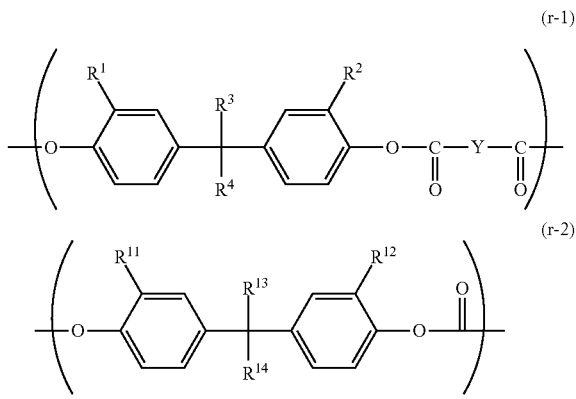

In general formulas (r-1) and (r-2), $R^1$, $R^2$, $R^{11}$, and $R^{12}$ each represent, independently of one another, a hydrogen atom or an alkyl group having a carbon number of at least 1 and no greater than 4. $R^3$, $R^4$, $R^{13}$, and $R^{14}$ each represent, independently of one another, a hydrogen atom, a phenyl group, or an alkyl group having a carbon number of at least 1 and no greater than 4. $R^3$ and $R^4$ may be bonded together to form a divalent group represented by general formula (W) shown below. $R^{13}$ and $R^{14}$ may be bonded together to form a divalent group represented by general formula (W) shown below. Y represents a divalent group represented by chemical formula (Y1), (Y2), (Y3), (Y4), (Y5), or (Y6) shown below.

(W)

In general formula (W), t represents an integer of at least 1 and no greater than 3. Asterisks each represent a bond.

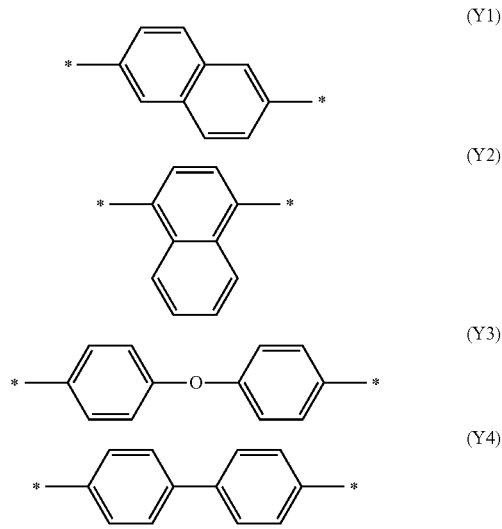

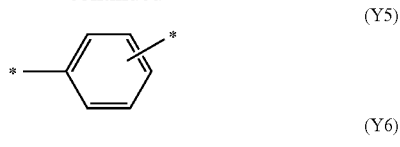
(Y5)

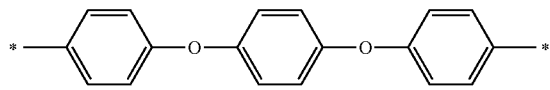
(Y6)

In chemical formulas (Y1) to (Y6), asterisks each represent a bond.

In general formulas (r-1) and (r-2), preferably, $R^1$, $R^2$, $R^{11}$, and $R^{12}$ each represent, independently of one another, a hydrogen atom or a methyl group. Furthermore, $R^1$ and $R^2$ are preferably the same as each other. Also, $R^{11}$ and $R^{12}$ are preferably the same as each other.

that one of $R^3$ and $R^4$ represents a methyl group and the other represents an ethyl group. Also, it is preferable that one of $R^{13}$ and $R^{14}$ represents a methyl group and the other represents an ethyl group. It is also preferable that $R^3$ and $R^4$ are bonded together to form a group represented by general formula (W). It is also preferable that $R^{13}$ and $R^{14}$ are bonded together to form a divalent group represented by general formula (W).

In general formula (W), t preferably represents 2.

In general formula (r-1), Y preferably represents a divalent group represented by chemical formula (Y1), (Y2), or (Y3).

The repeating unit represented by general formula (r-1) is preferably a repeating unit represented by any of chemical formulas (r-1a) to (r-1e) (also referred to below as repeating units (r-1a) to (r-1e), respectively) shown below.

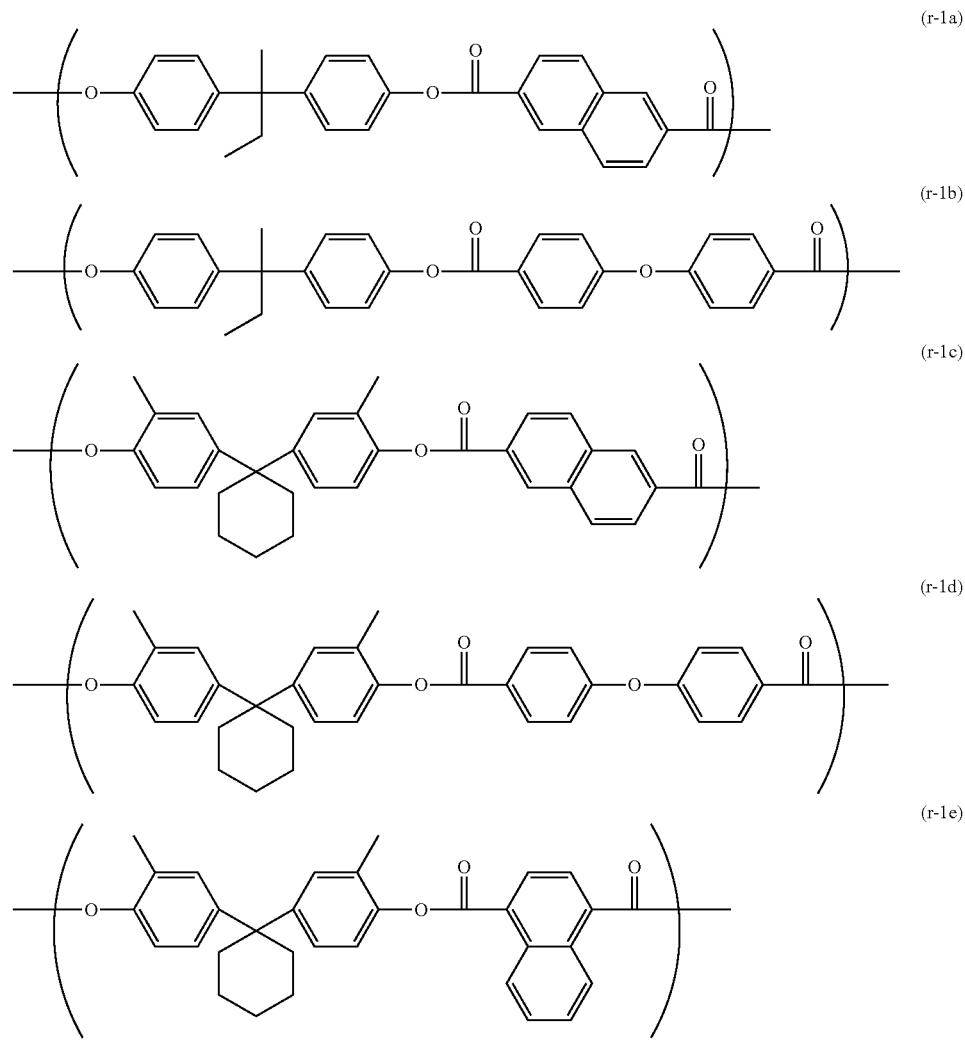

In general formulas (r-1) and (r-2), preferably, $R^3$, $R^4$, $R^{13}$, and $R^{14}$ each represent, independently of one another, a methyl group or an ethyl group. In a composition in which $R^3$, $R^4$, $R^{13}$, and $R^{14}$ each represent, independently of one another, a methyl group or an ethyl group, it is preferable Preferable polyarylate resins are: a polyarylate resin including the repeating unit (r-1a) and a repeating unit (r-1b); a polyarylate resin including a repeating unit (r-1c) and a repeating unit (r-1d); and polyarylate resin including the repeating unit (r-1c) and a repeating unit (r-1e).

Repeating units represented by chemical formulas (r-2a) and (r-2b) (also referred to below as repeating units (r-2a) and (r-2b), respectively) shown below are preferable as the repeating unit represented by general formula (r-2).

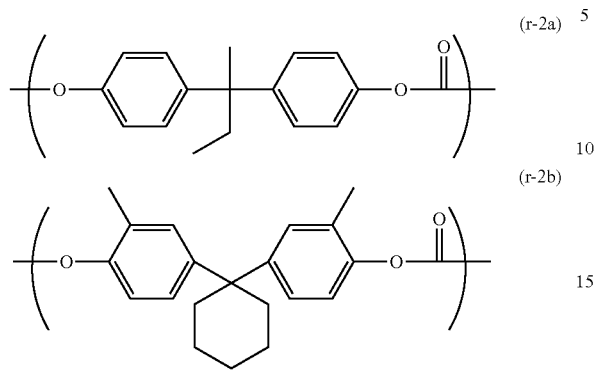

The binder resin preferably includes a polyarylate resin represented by chemical formula (R-1), (R-2), or (R-3) (also referred to below as polyarylate resins (R-1), (R-2), and (R-3)) shown below or a polycarbonate resin represented by chemical formula (R-4) or (R-5) (also referred to below as polycarbonates (R-4) and (R-5)) shown below. In chemical formulas (R-1) to (R-5), an index affixed to lower right of each repeating unit indicates a percentage of the number of the repeating unit to which the index is affixed relative to the total number of all repeating units included in the polyarylate resin or the polycarbonate resin. The polyarylate resins (R-1) to (R-3) and the polycarbonate resins (R-4) and (R-5) may each be a random copolymer, a block copolymer, a periodic copolymer, or an alternating copolymer.

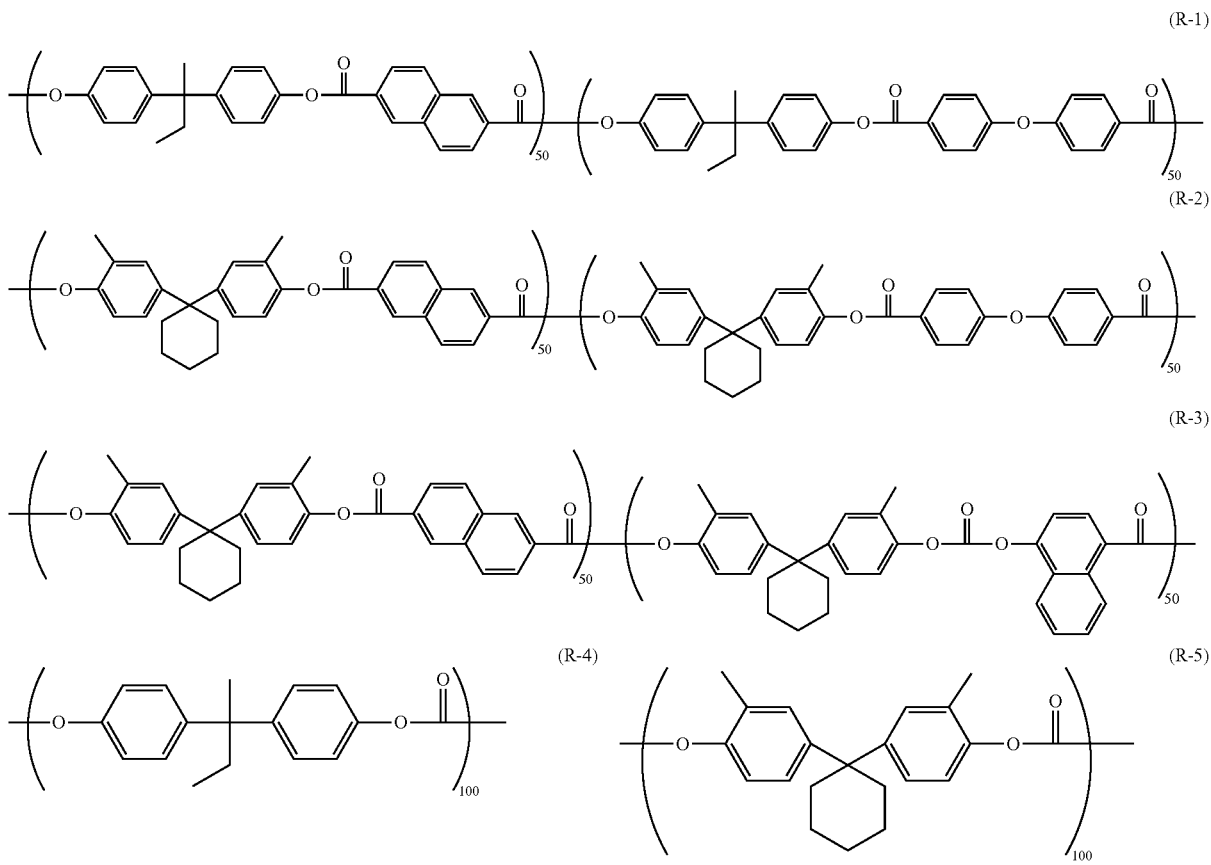

The binder resin preferably has a viscosity average molecular weight of at least 25,000, more preferably has a viscosity average molecular weight of at least 30,000 and no greater than 70,000, and further preferably has a viscosity average molecular weight of at least 45,000 and no greater than 54,000. As a result of the binder resin having a viscosity average molecular weight of at least 30,000, abrasion resistance of the photosensitive member 1 can be easily improved. As a result of the binder resin having a viscosity average molecular weight of no greater than 70,000, the binder resin can readily dissolve in a solvent in formation of the photosensitive layer 3, tending to appropriately reduce viscosity of an application liquid for charge transport layer formation or an application liquid for single-layer photosensitive layer formation. Thus, formation of the charge transport layer 3c or the single-layer photosensitive layer 3a can be facilitated.

(Base Resin)

In a situation in which the photosensitive member 1 is a multi-layer photosensitive member, the charge generating layer 3b contains a base resin. No particular limitations are placed on the base resin other than being applicable to the photosensitive member 1. Examples of the base resin include thermoplastic resins, thermosetting resins, and photocurable resins. Examples of thermoplastic resins include styrene-butadiene resins, styrene-acrylonitrile resins, styrene-maleate resins, styrene-acrylate resins, acrylic acid-based resins, polyethylene resins, ethylene-vinyl acetate resins, chlorinated polyethylene resins, polyvinyl chloride resins, polypropylene resins, ionomers, vinyl chloride-vinyl acetate resins, alkyd resins, polyamide resins, urethane resins, polycarbonate resins, polyarylate resins, polysulfone resins, diallyl phthalate resins, ketone resins, polyvinyl acetal resins, polyether resins, and polyester resins. Examples of thermosetting resins include silicone resins, epoxy resins, phenolic resins, urea resins, melamine resins, and other cross-linkable thermosetting resins. Examples of photocurable resins include epoxy-acrylate-based resins (specific examples include acrylic acid derivative adducts of epoxy compounds) and urethane-acrylate-based resins (specific examples include acrylic acid derivative adducts of urethane compounds). Any one of the base resins may be used independently, or any two or more of the base resins may be used in combination.

The base resin contained in the charge generating layer 3b is preferably different from the binder resin contained in the charge transport layer 3c. It is usual in multi-layer photosensitive member production that the charge generating layer 3b is formed on the conductive substrate 2 and the charge transport layer 3c is formed on the charge generating layer 3b. In multi-layer photosensitive member production as above, an application liquid for charge transport layer formation is applied onto the charge generating layer 3b in order to form the charge transport layer 3c. Therefore, when the base resin contained in the charge generating layer 3b is different from the binder resin contained in the charge transport layer 3c, the charge generating layer 3b is inhibited from dissolving in a solvent of the application liquid for charge transport layer formation in application of the application liquid for charge transport layer formation onto the charge generating layer 3b.

(Additive)

Each layer (the charge generating layer 3b, the charge transport layer 3c, and the single-layer photosensitive layer 3a) of the photosensitive layer 3 of the photosensitive member 1 may further contain various additives when necessary. Examples of the additives include antidegradants (specific examples include antioxidants, radical scavengers, quenchers, and ultraviolet absorbing agents), softeners, surface modifiers, extenders, thickeners, dispersion stabilizers, waxes, donors, surfactants, plasticizers, sensitizers, and leveling agents. Preferably, the charge transport layer 3c further contains an antioxidant as an additive.

In a situation in which the photosensitive member 1 is a multi-layer photosensitive member and the charge transport layer 3c thereof contains an antioxidant, the amount of the antioxidant in the charge transport layer 3c is preferably at least 0.05 parts by mass and no greater than 10 parts by mass relative to 100 parts by mass of the binder resin, and more preferably at least 0.1 parts by mass and no greater than 3 parts by mass.

(Combinations)

Combinations (j-1) to (j-9) listed in Table 1 below are preferable as a combination of the hole transport material and the binder resin in the photosensitive layer 3. Combinations (k-1) to (k-13) listed in Table 2 below are preferable as a combination of the hole transport material, the binder resin, and the electron transport material in the photosensitive layer 3.

TABLE 1

| Combination | Hole transport material | Binder resin |
|---|---|---|
| j-1 | HTM-1 | R-1 |
| j-2 | HTM-2 | R-1 |
| j-3 | HTM-3 | R-1 |
| j-4 | HTM-4 | R-1 |
| j-5 | HTM-5 | R-1 |
| j-6 | HTM-1 | R-2 |
| j-7 | HTM-1 | R-3 |
| j-8 | HTM-1 | R-4 |
| j-9 | HTM-1 | R-5 |

TABLE 2

| Combination | Hole transport material | Binder resin | Electron transport material |
|---|---|---|---|
| k-1 | HTM-1 | R-1 | ETM-1 |
| k-2 | HTM-2 | R-1 | ETM-1 |
| k-3 | HTM-3 | R-1 | ETM-1 |
| k-4 | HTM-4 | R-1 | ETM-1 |
| k-5 | HTM-5 | R-1 | ETM-1 |
| k-6 | HTM-1 | R-1 | ETM-2 |
| k-7 | HTM-1 | R-1 | ETM-3 |
| k-8 | HTM-1 | R-1 | ETM-4 |
| k-9 | HTM-1 | R-1 | ETM-5 |
| k-10 | HTM-1 | R-2 | ETM-1 |
| k-11 | HTM-1 | R-3 | ETM-1 |
| k-12 | HTM-1 | R-4 | ETM-1 |
| k-13 | HTM-1 | R-5 | ETM-1 |

[Intermediate Layer]

The intermediate layer 4 (an undercoat layer) contains for example inorganic particles and a resin (a resin for intermediate layer formation). It is thought that provision of the intermediate layer 4 facilitates flow of electric current generated when the photosensitive member 1 is exposed to light and inhibits increasing resistance, while also maintaining insulation to a sufficient degree so as to inhibit leakage current from occurring.

Examples of the inorganic particles include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one type of the inorganic particles listed above may be used independently, or any two or more types of the inorganic particles listed above may be used in combination.

No particular limitations are placed on the resin for intermediate layer formation other than being a resin that can be used for forming the intermediate layer 4. The intermediate layer 4 may contain various additives. Examples of the additives are the same as the additives listed for the photosensitive layer 3.

[Photosensitive Member Production Method]

The photosensitive member 1 that is a single-layer photosensitive member is produced for example by applying an application liquid for single-layer photosensitive layer formation onto the conductive substrate 2 to form a coating film and drying the coating film. The application liquid for single-layer photosensitive layer formation is prepared for example by dissolving or dispersing in a solvent a charge generating material, a binder resin, a charge transport material including the bis-butadiene derivative (1), and an additive that is to be added as necessary.

The photosensitive member 1 that is a multi-layer photosensitive member is produced for example as described below. First, an application liquid for charge generating layer formation and an application liquid for charge transport layer formation are prepared. The application liquid for charge generating layer formation is applied onto the conductive substrate 2 to form a coating film, and the coating film is dried to form the charge generating layer 3b. Next, the application liquid for charge transport layer formation is applied onto the charge generating layer 3b to form a coating film, and the coating film is dried to form the charge transport layer 3c. Through the above, the multi-layer photosensitive member is produced.

The application liquid for charge generating layer formation is prepared for example by dissolving or dispersing in a solvent a charge generating material, a base resin, and an additive that is to be added as necessary. The application liquid for charge transport layer formation is prepared by dissolving or dispersing in a solvent a binder resin, a charge transport material including the bis-butadiene derivative (1), and an additive that is to be added as necessary.

No particular limitations are placed on the respective solvents contained in the application liquid for single-layer photosensitive layer formation, the application liquid for charge generating layer formation, and the application liquid for charge transport layer formation (also referred collectively to below as application liquids) so long as the solvents can dissolve or disperse components included in the respective application liquids and can be removed from the respective coating films. Examples of the solvents include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. In order to improve workability in production of the photosensitive member 1, a non-halogen solvent (a solvent other than a halogenated hydrocarbon) is preferable as the solvents of the application liquids.

The application liquids are prepared by mixing corresponding components for dispersion in the respective solvents. A bead mill, a roll mill, a ball mill, an attritor, a paint shaker, or an ultrasonic disperser can be used for mixing and dispersion.

Each application liquid may contain for example a surfactant in order to improve dispersibility of the components.

No particular limitations are placed on a method by which each application liquid is applied so long as the method enables uniform application of the application liquid directly or indirectly onto a conductive substrate. Examples of the application method include dip coating, spray coating, spin coating, and bar coating.

No particular limitations are placed on a method by which the coating films are dried other than being a method that enables evaporation of the solvents contained in the respective application liquids. The method for drying each coating film may for example be heat treatment (hot-air drying) using a high-temperature dryer or a reduced pressure dryer. The heat treatment may be performed at a temperature of 40° or higher and 150° C. or lower. The heat treatment may be performed for example for 3 minutes or longer and 120 minutes or shorter.

The method for producing the photosensitive member 1 may further include either or both formation of the intermediate layer 4 and formation of the protective layer 5 as necessary. Any known methods are selected as appropriate for formation of the intermediate layer 4 and formation of the protective layer 5.

Fourth Embodiment: Bis-butadiene Halide Compound

A bis-butadiene halide compound according to a fourth embodiment of the present disclosure is represented by general formula (10) (also referred to below as a bis-butadiene halide compound (10)) shown below.

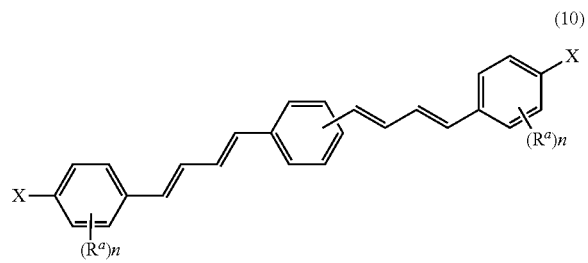

In general formula (10), $R^a$ represents an alkyl group having a carbon number of at least 1 and no greater than 8 or an alkoxy group having a carbon number of at least 1 and no greater than 8. n represents an integer of at least 0 and no greater than 4. X represents a halogen atom. Plural chemical groups $R^a$ may be the same as or different from each other. Plural indices n may be the same as or different from each other. Plural atoms X may be the same as or different from each other.

The bis-butadiene halide compound (10) can be used in production of the bis-butadiene derivative (1) according to the second embodiment of the present disclosure. That is, the bis-butadiene halide compound (10) can be used as a raw material compound of the bis-butadiene derivative (1) according to the first embodiment of the present disclosure.

Preferable groups that may be represented by $R^a$ and preferable numbers that may be represented by n in general formula (10) are respectively the same as the preferable groups that may be represented by $R^a$ and preferable numbers that are represented by n in general formula (1) described in the first embodiment.

In general formula (10), X preferably represents a chlorine atom or a bromine atom, and more preferably represents a chlorine atom.

Examples of the bis-butadiene halide compound (10) include compounds represented by general formulas (10-a), (10-b), and (10-c) shown below. Of the compounds represented by general formulas (10-a), (10-b), and (10-c), the compounds represented by general formulas (10-a) and (10-b) are preferable.

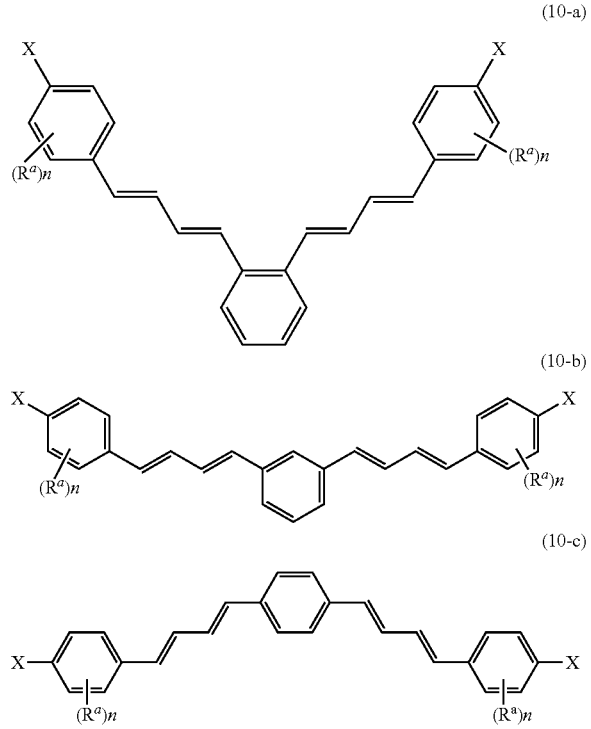

In general formulas (10-a), (10-b), and (10-c), $R^a$, n, and X are respectively the same as defined for $R^a$, n, and X in general formula (10).

Compounds represented by chemical formulas (10-1) and (10-2) (also referred to below as bis-butadiene halide compounds (10-1) and (10-2), respectively) are preferable as the bis-butadiene halide compound (10).

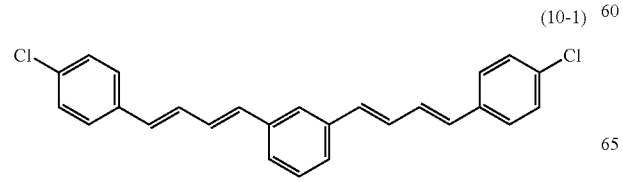

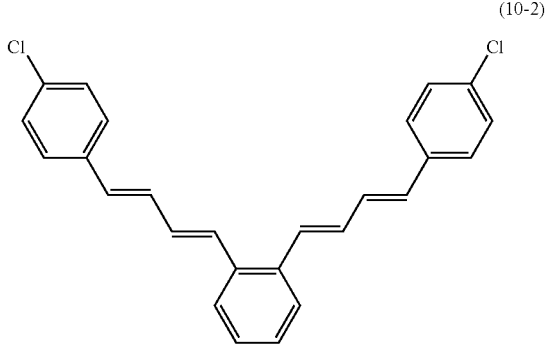

[Production Method of Bis-Butadiene Halide Compound (10)]

The bis-butadiene halide compound can be produced for example by a production method including carrying out reactions represented by chemical equations (Q-1) and (Q-2) (also referred to below as reactions (Q-1) and (Q-2), respectively) shown below. Hereinafter, compounds represented by general formulas (20), (22), and (23) in chemical equations (Q-1) and (Q-2) may be referred to below as compounds (20), (22), and (23), respectively.

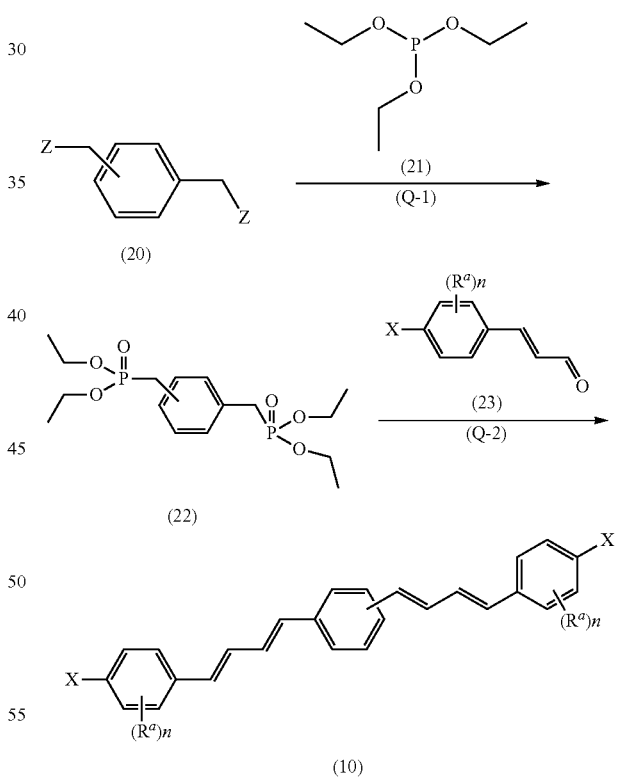

In chemical equations (Q-1) and (Q-2), $R^a$, X, and n are respectively the same as defined for $R^a$, X, and n in general formula (10). Z represents a halogen atom.

[Reaction (Q-1)]

In reaction (Q-1), a reaction between 1 mole equivalent of the compound (20) and 2 mole equivalents of triethyl phosphite represented by chemical formula (21) is caused to yield 1 mole equivalent of the compound (22). A molar ratio between the amount of the compound (20) and the amount of the triethyl phosphite (compound (20)/triethyl phosphite) in reaction (Q-1) is preferably at least 1/1.5 and no greater than 1/2.5. Reaction (Q-1) is carried out at a reaction temperature of 160° C. or higher and 200° C. or lower. Reaction time of reaction (Q-1) is preferably 2 hours or longer and 10 hours or shorter. Reaction (Q-1) is preferably carried out in an inert gas atmosphere (for example, in a nitrogen atmosphere).

[Reaction (Q-2)]

In reaction (Q-2), a reaction between 1 mole equivalent of the compound (22) and 2 mole equivalents of the compound (23) is caused to yield 1 mole equivalent of the bis-butadiene halide compound (10). In reaction (Q-2) in which the compound (23) is added, the compound (22) obtained through reaction (Q-1) may be used without purification. In the above case, a molar ratio between the amount of the compound (20) used in reaction (Q-1) and the amount of the compound (23) used in reaction (Q-2) (compound (20)/compound (23)) is preferably at least 1/2 and no greater than 1/6.

Reaction (Q-2) is preferably carried out at a reaction temperature of 0° C. or higher and 50° C. or lower. Reaction time of reaction (Q-2) is preferably 2 hours or longer and 24 hours or shorter.

Reaction (Q-2) may be carried out in the presence of a base. Examples of the base include sodium alkoxides (specific examples include sodium methoxide, sodium ethoxide, and sodium butoxide), metal hydrides (specific examples include sodium hydride and potassium hydride), and metal salts (specific examples include n-butyl lithium). Sodium alkoxides are preferable as the base, and sodium butoxide is more preferable. Any one of the bases listed above may be used independently, or any two or more of the bases listed above may be used in combination. A preferable amount of the base is at least 0.5 mol and no greater than 1.5 mol relative to 1 mole of the compound (23).

The same solvents listed as the solvents that can be used in reaction (P) can be used as a solvent in reaction (Q-2), and dimethyl formamide is preferable.

The bis-butadiene halide compound (10) obtained through reaction (Q-2) may be purified as necessary. Examples of purification methods include known methods (for example, filtering, silica gel chromatography, and crystallization).

EXAMPLES

The following further describes the present disclosure in detail using examples. However, the present disclosure is by no means limited to the following examples.

The following hole transport materials, binder resins, and electron accepting compounds were prepared as materials for forming charge transport layers of multi-layer photosensitive members.

(Hole Transport Material)

The bis-butadiene derives (HTM-1) to (HTM-5) described in the first embodiment were prepared as the hole transport materials. The following describes their synthesis methods.

In synthesis of the bis-butadiene derivative (HTM-1), the bis-butadiene halide compound (10-1) described in the fourth embodiment was used as a raw material compound. A synthesis method of the bis-butadiene halide compound (10-1) is described first.

(Synthesis of Bis-Butadiene Halide Compound (10-1))

A 500-mL two-necked flask was charged with 17.51 g (0.1 mol) of α,α'-dichloro-m-xylene represented by chemical formula (20-1) shown below and 34.89 g (0.21 mol) of triethyl phosphite represented by chemical formula (21) shown below. The resultant reaction solution was stirred for 4 hours at 180° C. under nitrogen purge, and then cooled to room temperature. Through the above, a compound represented by chemical formula (22-1) shown below was obtained. Into the reaction solution thus obtained, 94.7 g of dehydrated dimethyl formamide (dehydrated DMF) was added. The reaction solution was then cooled to −20° C. After 31.68 g (0.33 mol) of sodium butoxide was added to the reaction solution, the reaction solution was stirred for 10 minutes while being kept at a temperature of −20° C. or higher and 0° C. or lower.

After the stirring, 155.27 g of a DMF solution of 4-chlorocinnamaldehyde represented by chemical formula (23-1) shown below (a solution of approximately 85 g of dehydrated DMF in which 69.97 g (0.42 mol) of 4-chlorocinnamaldehyde had been pre-dissolved) was added to the reaction solution. Then, the resultant reaction solution was stirred for 12 hours at room temperature. The resultant mixture was added into a 1-L conical flask containing 252.3 g of an aqueous hydrochloric acid solution (mixed liquid of 31.3 g (0.3 mol) of 35% hydrochloric acid and 221 g of ion exchanged water). The two-necked flask that had contained the reaction solution was then washed with tetrahydrofuran (THF), and the THF used for the washing was further charged into the conical flask.

A precipitated solid was filtered off, and a residue was washed with methanol. The filtration and the washing were repeated until a filtrate became transparent. A residue after the final washing was dried using a vacuum oven for 24 hours at 70° C. to obtain 19.9 g of a bis-butadiene halide compound (10-1) represented by chemical formula (10-1) shown below (percentage yield 49.3%). A series of reactions is shown by the following chemical equations (Q-1) and (Q-2).

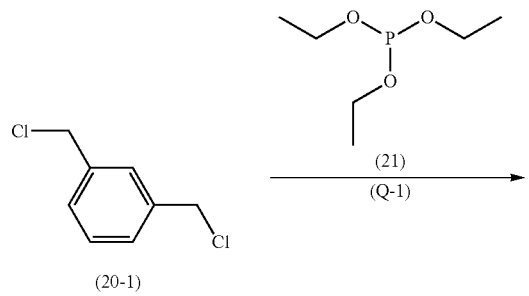

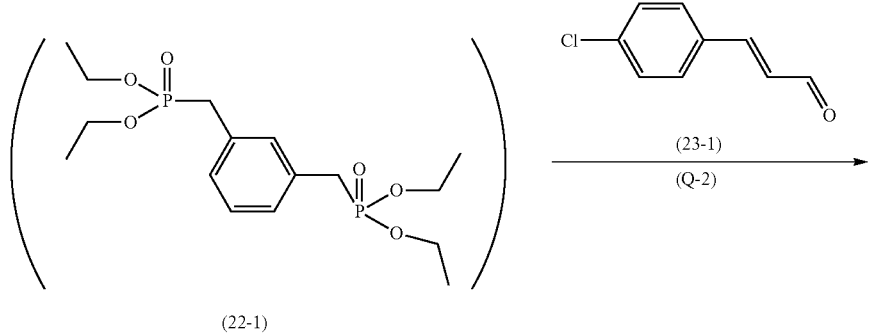

(22-1) (23-1) (Q-2)

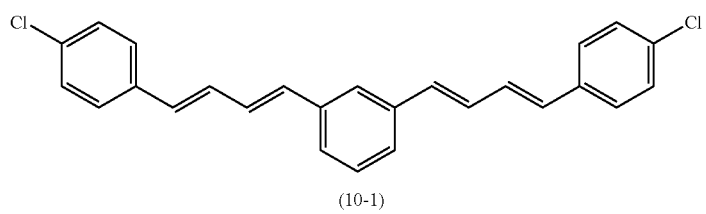

(10-1)

The following describes a synthesis method of the bis-butadiene derivative (HTM-1) of which a raw material compound is the bis-butadiene halide compound (10-1).

(Synthesis of Bis-Butadiene Derivative (HTM-1)).

A 500-mL two-necked flask was charged with 8.067 g (0.02 mol) of the bis-butadiene halide compound (10-1) obtained by the above method, 8.429 g (0.046 mol) of 4-methyldiphenylamine represented by chemical formula (11-1) shown below, 0.229 g (0.00048 mol) of 2-dicyclohexylphosphino-2',4',6'-triisopropylbiphenyl, 0.027 g (0.00012 mol) of palladium acetate, 4.992 g (0.052 ml) of sodium tert-butoxide, and 75 g of mixed xylene. Then, the inside of the two-necked flask was purged with a nitrogen gas. Thereafter, the reaction liquid in the two-necked flask was stirred for 5 hours at 150° C. and then cooled to 70° C. Furthermore, 4.2 g of an activated clay ("SA-1", product of Toshin Chemicals Co., Ltd.) was added to the reaction liquid, and the reaction liquid was stirred for 10 minutes while being kept at 70° C. Hot filtration was performed (first time) on the reaction liquid kept at 70° C., and a filtrate from which the activated clay and insoluble matter had been removed was collected. Thereafter, 16.8 g of an activated clay ("SA-1", product of Toshin Chemicals Co., Ltd.) was added to the filtrate and the resultant filtrate was stirred for 10 minutes at 70° C. Filtration was performed (second time) again on the filtrate after the stirring, and a filtrate was collected.

Thereafter, xylene was removed, using an evaporator, from the filtrate collected after the second-time filtration. The resultant residue was dissolved in 50 g of THF, and the THF in which the residue had been dissolved was dripped into 250 g of isopropanol to filter off a precipitate. The thus collected precipitate was purified by column chromatography using toluene and n-hexane as a developing solvent to yield 10.0 g of a bis-butadiene derivative (HTM-1) represented by chemical formula (HTM-1) shown below (percentage yield 71.7%). A series of reactions is shown by the following chemical equation (P-1).

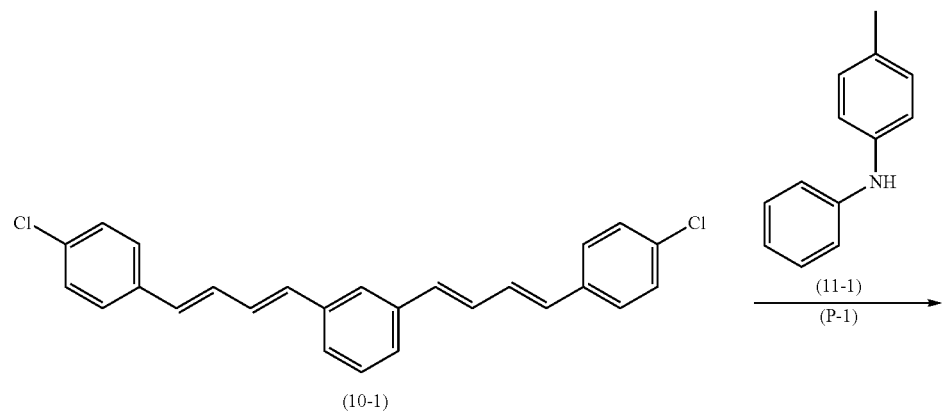

(10-1) (11-1) (P-1)

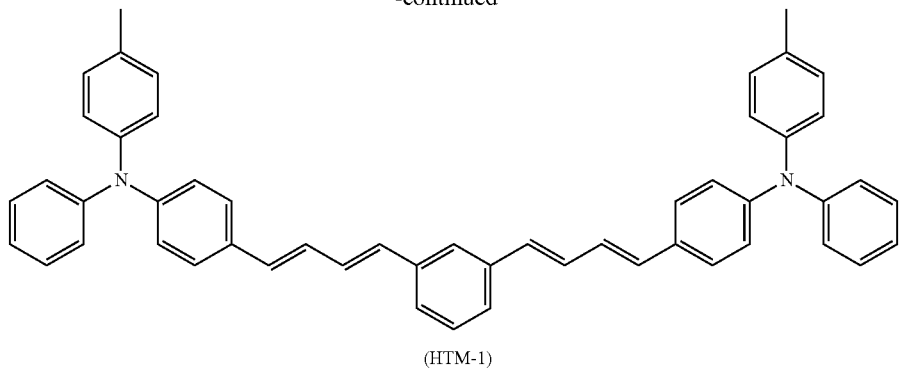

(HTM-1)

(Synthesis of Bis-Butadiene Halide Compound (10-2))

The bis-butadiene halide compound (10-2) represented by chemical formula (10-2) shown below was synthesized by the same method as for the bis-butadiene halide compound (10-1) in all aspects other than the following change. Specifically, the bis-butadiene halide compound (10-2) was synthesized using 17.51 g (0.1 mol) of α,α'-dichloro-o-xylene represented by chemical formula (20-2) shown below instead of α,α'-dichloro-m-xylene. As a result, 17.5 g of the bis-butadiene halide compound (10-2) was obtained (percentage yield 43.4%).

Note that the number of moles of each raw material used in synthesis of the bis-butadiene halide compound (10-2) was the same as the number of moles of a corresponding one of the raw materials used in synthesis of the bis-butadiene halide compound (10-1).

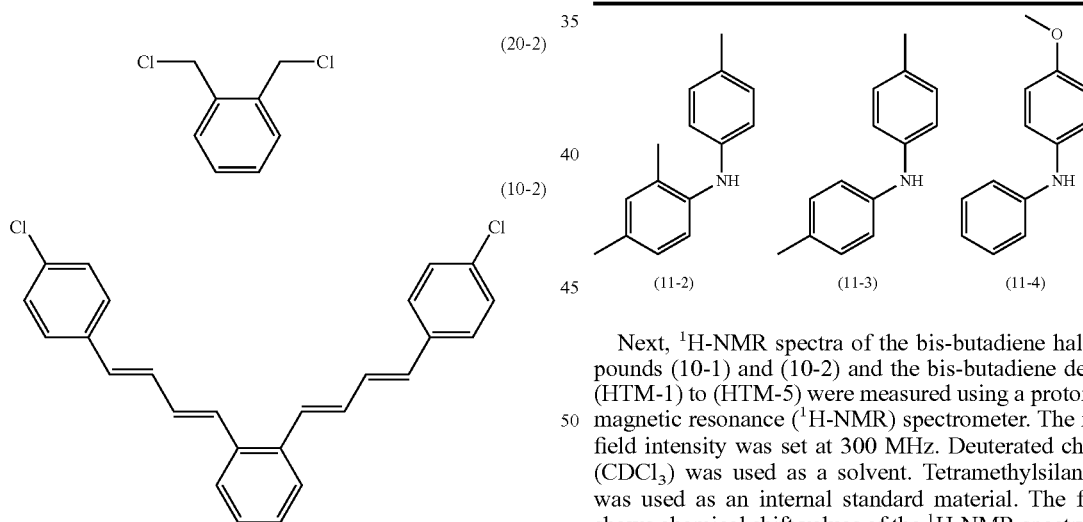

(20-2)

(10-2)

(Synthesis of Bis-Butadiene Derivatives (HTM-2) to (HTM-5))

The bis-butadiene derivatives (HTM-2) to (HTM-5) were synthesized by the same method as for the bis-butadiene derivative (HTM-1) in all aspects other than the following changes. Specifically, in synthesis of the bis-butadiene derivatives (HTM-2) to (HTM-5), the compounds represented by chemical formulas (10-1) and (11-1) were changed to compounds of types and amounts shown in Table 3 below. Mass yields and percentage yields resulting from the respective synthesis reactions of the bis-butadiene derivatives (HTM-1) to (HTM-5) are shown in Table 3 below.

Note that the number of moles of each raw material used in syntheses of the bis-butadiene derivatives (HTM-2) to (HTM-5) was the same as the number of moles of a corresponding one of the raw materials used in synthesis of the bis-butadiene derivative (HTM-1).

TABLE 3

| Bis-butadiene derivative | Bis-butadiene halide compound (10) | | Compound (11) | | Mass yield [g] | Percentage yield [%] |
| --- | --- | --- | --- | --- | --- | --- |
| | Type | Amount [g] | Type | Amount [g] | | |
| HTM-1 | 10-1 | 8.067 | 11-1 | 8.429 | 10.0 | 71.7 |
| HTM-2 | 10-1 | 8.067 | 11-2 | 9.702 | 10.6 | 70.4 |
| HTM-3 | 10-2 | 8.067 | 11-1 | 8.429 | 10.4 | 74.6 |
| HTM-4 | 10-2 | 8.067 | 11-3 | 9.075 | 10.5 | 72.4 |
| HTM-5 | 10-2 | 8.067 | 11-4 | 9.166 | 9.8 | 67.2 |

(11-2)            (11-3)            (11-4)

Next, $^1$H-NMR spectra of the bis-butadiene halide compounds (10-1) and (10-2) and the bis-butadiene derivatives (HTM-1) to (HTM-5) were measured using a proton nuclear magnetic resonance ($^1$H-NMR) spectrometer. The magnetic field intensity was set at 300 MHz. Deuterated chloroform (CDCl$_3$) was used as a solvent. Tetramethylsilane (TMS) was used as an internal standard material. The following shows chemical shift values of the $^1$H-NMR spectrum of the bis-butadiene halide compound (10-1) as a representative of the bis-butadiene halide compounds (10-1) and (10-2). The following also shows chemical shift values of the $^1$H-NMR spectrum of the bis-butadiene derivative (HTM-1) as a reprehensive of the bis-butadiene derivatives (HTM-1) to (HTM-5). The chemical shift values of the measured $^1$H-NMR spectra were used to confirm that the bis-butadiene halide compound (10-1) and the bis-butadiene derivative (HTM-1) had been obtained. As for the bis-butadiene halide compound (10-2) and the bis-butadiene derivatives (HTM-2) to (HTM-5), the chemical shift values of the respective measured $^1$H-NMR spectra were used to confirm that these compounds had been obtained.

Bis-butadiene halide compound (10-1): $^1$H-NMR (300 MHz, CDCl$_3$) δ=7.44 (s, 1H), 7.20-7.36 (m, 15H), 6.94-7.09 (m, 2H), 6.65-6.80 (m, 2H)

Bis-butadiene derivative (HTM-1): $^1$H-NMR (300 MHz, CDCl$_3$) δ=7.46 (s, 1H), 7.21-7.31 (m, 11H), 6.95-7.11 (m, 20H), 6.79-6.93 (m, 3H), 6.58-6.65 (m, 3H), 2.32 (s, 6H)

Compounds represented by chemical formulas (h-1) to (h-3) (also referred to below as hole transport materials (h-1) to (h-3), respectively) shown below were prepared as hole transport materials used for Comparative Examples.

Polycarbonate resin (R-4): 53,400
Polycarbonate resin (R-5): 50,900

(Electron Acceptor Compound)

The compounds (ETM-1) to (ETM-5) described in the third embodiment were prepared as the electron acceptor compounds.

[Production of Photosensitive Member (A-1)]

The following describes a production method of the photosensitive member (A-1) of Example 1.

(Intermediate Layer Formation)

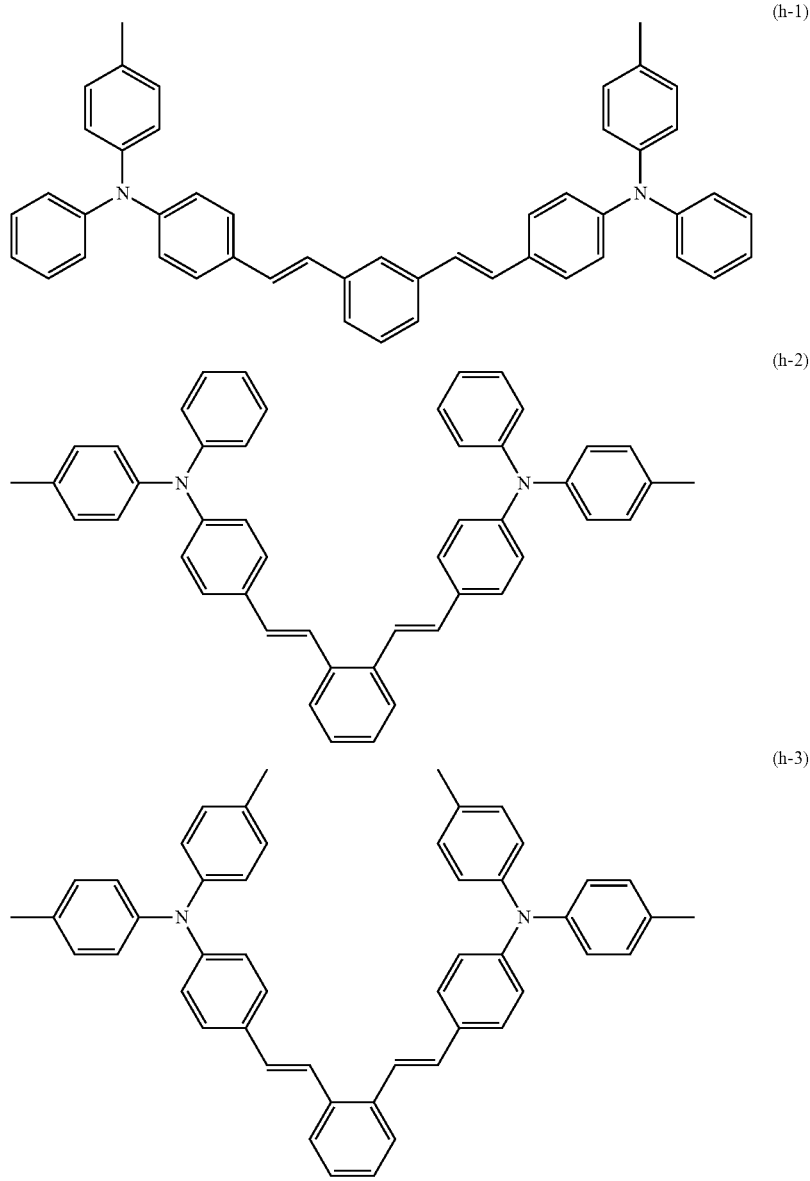

(Binder Resin)

The polyarylate resins (R-1) to (R-3) and the polycarbonate resins (R-4) and (R-5) described in the third embodiment were prepared as the binder resins. The viscosity average molecular weight of each resin was shown below.

Polyarylate resin (R-1): 50,500
Polyarylate resin (R-2): 50,100
Polyarylate resin (R-3): 48,300

First, surface-treated titanium oxide ("SMT-A (trial product)", product of Tayca Corporation, number-average primary particle size: 10 nm) was prepared. Specifically, the surface treated titanium oxide was prepared through surface treatment on titanium oxide with alumina and silica and surface treatment with methyl hydrogen polysiloxane under wet-dispersion of the titanium oxide subjected to surface treatment. Next, the surface-treated titanium oxide (2 parts by mass) and a polyamide resin ("AMILAN (registered Japanese trademark) CM8000", product of Toray Industries, Inc., 1 part by mass) were added to a combined solvent. The combined solvent contained methanol (10 parts by mass), butanol (1 part by mass), and toluene (1 apart by mass). The polyamide resin was a quarterpolymer polyamide resin composed of polyamide 6, polyamide 12, polyamide 66, and polyamide 610. These materials (the surface-treated titanium oxide and the polyamide resin) were dispersed in the combined solvent by mixing for 5 hours using a bead mill. Through the above process, an application liquid for intermediate layer formation was prepared.

The resultant application liquid for intermediate layer formation was filtered using a filter having a pore size of 5 μm. Thereafter, the application liquid for intermediate layer formation was applied onto the surface of a conductive substrate by dip coating to form a coating film. The conductive substrate was a drum-shaped aluminum support (diameter 30 mm, total length 246 mm). Next, the coating film was dried for 30 minutes at 130° C., thereby forming an intermediate layer (film thickness 2 μm) on the conductive substrate.

(Charge Generating Layer Formation)

Y-form titanyl phthalocyanine (1.5 parts by mass) and a polyvinyl acetal resin ("S-LEC BX-5", product of Sekisui Chemical Co., Ltd., 1 part by mass) as a base resin were added to a combined solvent. The combined solvent included propylene glycol monomethyl ether (40 parts by mass) and tetrahydrofuran (40 parts by mass). The materials (the Y-form titanyl phthalocyanine and the polyvinyl acetal resin) were mixed for 2 hours using a bead mill to disperse the materials in the combined solvent. Through the above process, an application liquid for charge generating layer formation was prepared.

The resultant application liquid for charge generating layer formation was filtered using a filter having a pore size of 3 μm. After the filtration, the resultant filtrate was applied onto the intermediate layer formed as described above by dip coating to form a coating film. The coating film was dried for 5 minutes at 50° C. Through the above process, a charge generating layer (film thickness 0.3 μm) was formed on the intermediate layer.

(Charge Transport Layer Formation)

To a combined solvent, 60 parts by mass of the bis-butadiene derivative (HTM-1) as a hole transport material, 0.5 parts by mass of an antioxidant ("IRGANOX (registered Japanese trademark) 1010", product of BASF) as an additive, 2 parts by mass of the compound (ETM-1) as an electron acceptor compound, 100 parts by mass of the polyarylate resin (R-1) (viscosity average molecular weight: 50,500) as a binder resin, and 0.05 parts by mass of dimethyl silicone oil ("K-96-50CS", product of Shin-Etsu Chemical Co., Ltd.) as a leveling agent were added. The combined solvent contained 350 parts by mass of tetrahydrofuran (THF) and 350 parts by mass of toluene. These materials (the hole transport material, the additive, the electron acceptor compound, and the polyarylate resin) were mixed with the combined solvent to be dispersed in the combined solvent, thereby preparing an application liquid for charge transport layer formation.

By the same scheme as that using the application liquid for charge generating layer formation, the application liquid for charge transport layer formation was applied onto the charge generating layer to form a coating film. Next, the coating film was dried for 40 minutes at 120° C. to form a charge transport layer (film thickness 20 μm) on the charge generating layer. The multi-layer photosensitive member (A-1) was obtained as a result of the process described above. The photosensitive member (A-1) had a structure in which the intermediate layer, the charge generating layer, and the charge transport layer were layered on the conductive substrate in the state order.

[Production of Photosensitive Members (A-2) to (A-13) and (B-1) to (B-3)]

Photosensitive members (A-2) to (A-13) and (B-1) to (B-3) were produced by the same method as for the photosensitive member (A-1) in all aspects other than the following changes. Specifically, while the bis-butadiene derivative (HTM-1) was used as a hole transport material in production of the photosensitive member (A-1), hole transport materials of types shown in Table 4 below were used in production of the respective photosensitive members (A-2) to (A-13) and (B-1) to (B-3). While the polyarylate resin (R-1) was used as a binder resin in production of the photosensitive member (A-1), resins of types shown in Table 4 below were used in production of the respective photosensitive members (A-2) to (A-13) and (B-1) to (B-3). Also, while the compound (ETM-1) was used as an electron transport material in production of the photosensitive member (A-1), electron transport materials of types shown in Table 4 below were used in production of the respective photosensitive members (A-2) to (A-13) and (B-1) to (B-3). HTM-1 to HTM-5 in a column titled "Hole transport material" in Table 4 below represent the bis-butadiene derivatives (HTM-1) to (HTM-5), respectively.

Electrical characteristics (charge characteristic and sensitivity characteristic) were measured by methods described below for each of the photosensitive members (A-1) to (A-13) and (B-1) to (B-3). The results of measurement are shown in Table 4 below.

<Measurement of Charge Characteristic>

With respect to each of the photosensitive members (A-1) to (A-13) and (B-1) to (B-3), a charge characteristic was measured in an environment at a temperature of 10° C. and a relative humidity of 20% RH. Specifically, the multi-layer photosensitive member was charged using a drum sensitivity test device (product of Gen-Tech, Inc.) under conditions of a rotational speed of the multi-layer photosensitive member of 31 rpm and an electric current flowing into the multi-layer photosensitive member of −10 μA. The surface potential of the thus charged photosensitive member was measured. The measured surface potential was taken to be a charge potential $V_O$ (unit: −V) of the photosensitive member.

<Measurement of Sensitivity Characteristic>

With respect to each of the photosensitive members (A-1) to (A-13) and (B-1) to (B-3), a sensitivity characteristic was measured in an environment at a temperature of 10° C. and a relative humidity of 20% RH. Specifically, the surface of the photosensitive member was charged to −600 V using a drum sensitivity test device (product of Gen-Tech, Inc.). Next, monochromatic light (wavelength: 780 nm, exposure amount: 0.26 μJ/cm$^2$) was taken out from light of a halogen lamp using a bandpass filter and irradiation therewith was performed on the surface of the photosensitive member. The surface potential of the photosensitive member was measured when 50 milliseconds elapsed after completion of the irradiation with the monochromatic light. The measured surface potential was taken to be a post-exposure potential $V_L$ (unit: V) of the photosensitive member.

TABLE 4

| | Photosensitive member | Hole transport material | Binder resin | Electron transport material | Electrical characteristic $V_0$ [−V] | $V_L$ [−V] |
|---|---|---|---|---|---|---|
| Example 1 | A-1 | HTM-1 | R-1 | ETM-1 | 684 | 48 |
| Example 2 | A-2 | HTM-2 | R-1 | ETM-1 | 684 | 45 |
| Example 3 | A-3 | HTM-3 | R-1 | ETM-1 | 684 | 60 |
| Example 4 | A-4 | HTM-4 | R-1 | ETM-1 | 679 | 45 |
| Example 5 | A-5 | HTM-5 | R-1 | ETM-1 | 675 | 58 |
| Example 6 | A-6 | HTM-1 | R-1 | ETM-2 | 674 | 46 |
| Example 7 | A-7 | HTM-1 | R-1 | ETM-3 | 684 | 43 |
| Example 8 | A-8 | HTM-1 | R-1 | ETM-4 | 685 | 50 |
| Example 9 | A-9 | HTM-1 | R-1 | ETM-5 | 669 | 46 |
| Example 10 | A-10 | HTM-1 | R-2 | ETM-1 | 685 | 44 |
| Example 11 | A-11 | HTM-1 | R-3 | ETM-1 | 684 | 49 |
| Example 12 | A-12 | HTM-1 | R-4 | ETM-1 | 681 | 44 |
| Example 13 | A-13 | HTM-1 | R-5 | ETM-1 | 674 | 47 |
| Comparative Example 1 | B-1 | h-1 | R-1 | ETM-1 | 680 | 86 |
| Comparative Example 2 | B-2 | h-2 | R-1 | ETM-1 | 676 | 110 |
| Comparative Example 3 | B-3 | h-3 | R-1 | ETM-1 | 684 | 85 |

The bis-butadiene derivatives (HTM-1) to (HTM-5) each were a compound represented by general formula (1). The photosensitive members (A-1) to (A-13) each included a conductive substrate and a photosensitive layer located indirectly on the conductive substrate. The photosensitive layer contained a charge generating material, a charge transport material, and a binder resin. The charge transport material included any of the bis-butadiene derivatives (HTM-1) to (HTM-5).

By contrast, the photosensitive layers of the photosensitive members (B-1) to (B-3) did not contain the bis-butadiene derivative (1). Specifically, the photosensitive layers of the photosensitive members (B-1) to (B-3) respectively contained the compounds (h-1) to (h-3), each of which was not a compound represented by general formula (1).

As evident from Table 4, the photosensitive members (A-1) to (A-13) each had a smaller absolute value of the post-exposure potential $V_L$ than the photosensitive members (B-1) to (B-3) of Comparative Examples, and therefore, were excellent in sensitivity characteristic.

From the above, it is understood that use of the bis-butadiene derivative according to the present disclosure can improve the sensitivity characteristic of a photosensitive member more than use of any known hole transport materials. Furthermore, it is understood that the photosensitive member according to the present disclosure is more excellent in sensitivity characteristic than any known photosensitive members. Also, it is understood that the bis-butadiene derivative production method according to the present disclosure can implement efficient production of the above bis-butadiene derivative. It is still understood that the bis-butadiene halide compound according to the present disclosure can be used in the above bis-butadiene derivative production method.

What is claimed is:

1. An electrophotographic photosensitive member comprising:
    a conductive substrate; and a photosensitive layer located either directly or indirectly on the conductive substrate, wherein
    the photosensitive layer contains at least a charge generating material, a charge transport material, and a binder resin,
    the charge transport material includes a hole transport material,
    the hole transport material is only one of bis-butadiene derivatives represented by chemical formulas (HTM-1), (HTM-2), (HTM-3), and (HTM-5) shown below, and
    the binder resin includes
        a polyarylate resin including a repeating unit represented by chemical formula (r-1c) shown below and a repeating unit represented by chemical formula (r-1d) shown below, or
        a polycarbonate resin including a repeating unit represented by chemical formula (r-2a) shown below:

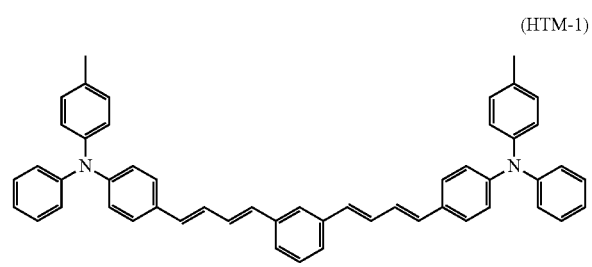
(HTM-1)

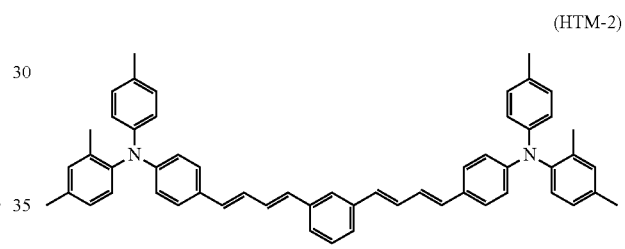
(HTM-2)

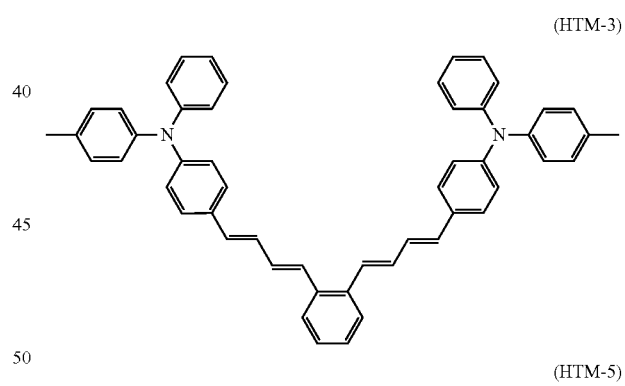
(HTM-3)

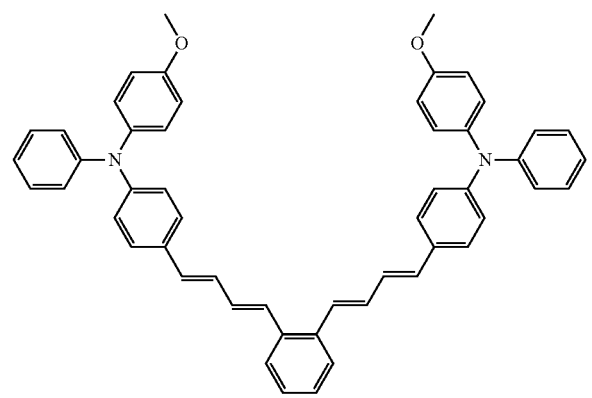
(HTM-5)

-continued (r-1c)
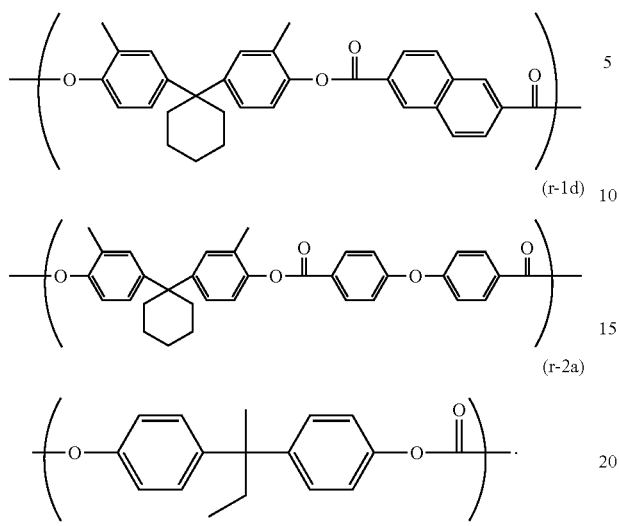

(r-1d)

(r-2a)

2. The electrophotographic photosensitive member according to claim 1, wherein
the photosensitive layer includes a charge generating layer and a charge transport layer,
the charge generating layer contains the charge generating material, and
the charge transport layer contains at least the charge transport material and the binder resin.

3. The electrophotographic photosensitive member according to claim 2, wherein
the charge transport layer further contains a compound represented by any of general formulas (E-1) to (E-4) shown below:

(E-1)
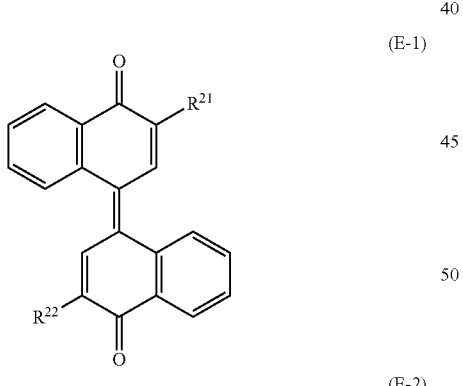

(E-2)
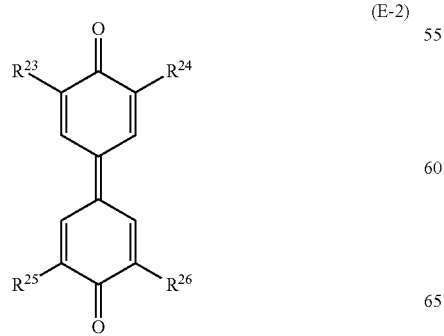

(E-3)
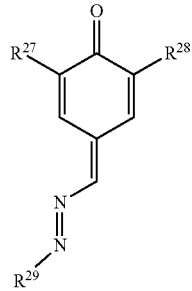

(E-4)
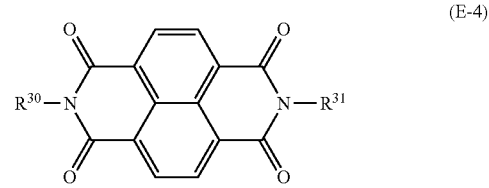

where in the general formula (E-1), $R^{21}$ and $R^{22}$ each represent, independently of one another, an alkyl group having a carbon number of at least 1 and no greater than 6, an alkoxy group having a carbon number of at least 1 and no greater than 6, an aryl group having a carbon number of at least 6 and no greater than 14, or an aralkyl group having a carbon number of at least 7 and no greater than 20, in the general formula (E-2), $R^{23}$, $R^{24}$, $R^{25}$, and $R^{26}$ each represent, independently of one another, an alkyl group having a carbon number of at least 1 and no greater than 6, in the general formula (E-3), $R^{27}$ and $R^{28}$ each represent, independently of one another, an alkyl group having a carbon number of at least 1 and no greater than 6, and $R^{29}$ represents an aryl group having a carbon number of at least 6 and no greater than 14 and optionally substituted by a halogen atom, and in the general formula (E-4), $R^{30}$ and $R^{31}$ each represent, independently of one another, an aryl group having a carbon number of at least 6 and no greater than 14 and optionally substituted by an alkyl group having a carbon number of at least 1 and no greater than 4.

4. The electrophotographic photosensitive member according to claim 3, wherein
the compound represented by the general formula (E-1) is represented by chemical formula (ETM-1) shown below, the compound represented by the general formula (E-2) is represented by chemical formula (ETM-2) or (ETM-3) shown below, the compound represented by the general formula (E-3) is represented by chemical formula (ETM-4) shown below, and the compound represented by the general formula (E-4) is represented by chemical formula (ETM-5) shown below:

(ETM-1)
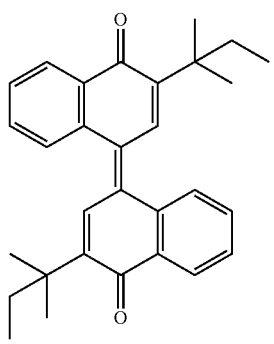

(ETM-2)
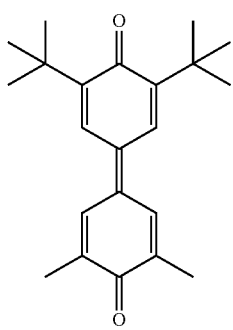

(ETM-3)
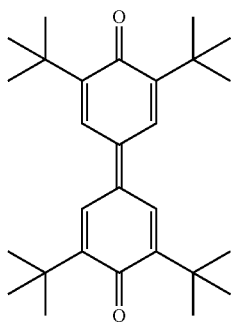

(ETM-4)
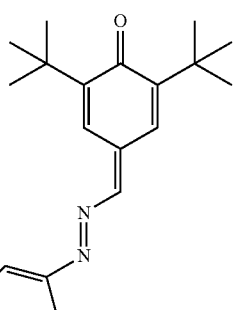

(ETM-5)
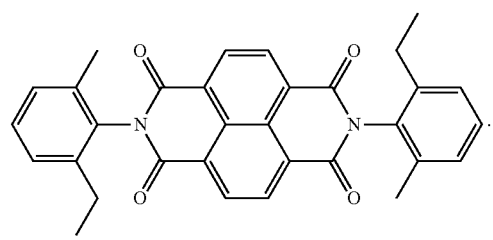

5. The electrophotographic photosensitive member according to claim 1, wherein
the binder resin includes the polyarylate resin including the repeating unit represented by the chemical formula (r-1c) and the repeating unit represented by the chemical formula (r-1d).

6. The electrophotographic photosensitive member according to claim 1, wherein
the binder resin includes a polyarylate resin represented by chemical formula (R-2) shown below:

(R-2)
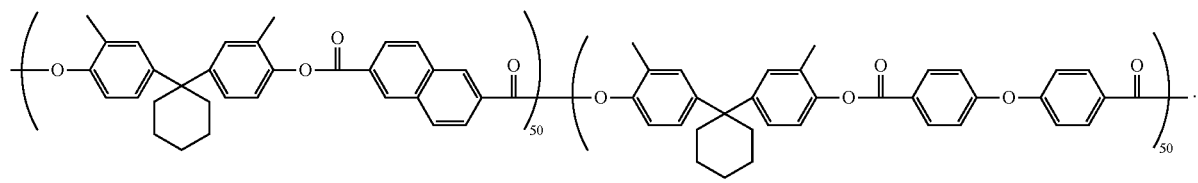

7. The electrophotographic photosensitive member according to claim 1, wherein
the binder resin includes the polycarbonate resin including the repeating unit represented by the chemical formula (r-2a).

8. The electrophotographic photosensitive member according to claim 1, wherein
the binder resin includes a polycarbonate resin represented by chemical formula (R-4) shown below:

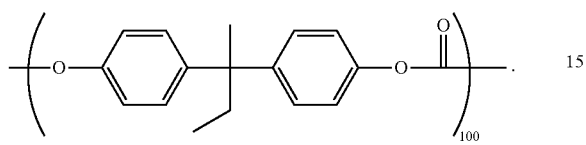

* * * * *